US006844404B2

(12) United States Patent
Ponasik, Jr. et al.

(10) Patent No.: US 6,844,404 B2
(45) Date of Patent: Jan. 18, 2005

(54) CATALYST COMPOSITIONS FOR THE POLYMERIZATION OF OLEFINS

(75) Inventors: James Allen Ponasik, Jr., Kingsport, TN (US); Jason Patrick McDevitt, Wake Forest, NC (US); Christopher Moore Killian, Gray, TN (US); Peter Borden Mackenzie, Kingsport, TN (US); Leslie Shane Moody, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 104 days.

(21) Appl. No.: 09/776,984

(22) Filed: Feb. 5, 2001

(65) Prior Publication Data

US 2002/0035030 A1 Mar. 21, 2002

Related U.S. Application Data

(60) Division of application No. 09/222,614, filed on Dec. 29, 1998, now Pat. No. 6,200,925, which is a continuation-in-part of application No. 09/028,315, filed on Feb. 24, 1998, now abandoned.
(60) Provisional application No. 60/045,697, filed on May 6, 1997, provisional application No. 60/045,358, filed on May 2, 1997, provisional application No. 60/045,357, filed on May 2, 1997, provisional application No. 60/045,337, filed on May 1, 1997, provisional application No. 60/044,691, filed on Apr. 18, 1997, and provisional application No. 60/040,754, filed on Mar. 13, 1997.

(51) Int. Cl.$^7$ ............... C08F 4/70; C08F 4/80

(52) U.S. Cl. ............... 526/172; 526/161; 526/169.1; 526/171; 526/134

(58) Field of Search .............. 526/161, 169.1, 526/171, 172, 134

(56) References Cited

U.S. PATENT DOCUMENTS

| | | | |
|---|---|---|---|
| 4,689,437 A | 8/1987 | Murray | |
| 4,691,036 A | 9/1987 | Starzewski et al. | |
| 4,716,138 A | 12/1987 | Murray | |
| 4,716,205 A | 12/1987 | Klabunde | |
| 4,724,273 A | 2/1988 | Fink et al. | |
| 4,906,754 A | 3/1990 | Klabunde | |
| 5,030,606 A | 7/1991 | Klabunde | |
| 5,175,326 A | 12/1992 | Klabunde | |
| 5,714,556 A | 2/1998 | Johnson et al. | |
| 5,852,145 A | 12/1998 | McLain et al. | |
| 5,866,663 A | 2/1999 | Brookhart et al. | |
| 5,880,241 A | 3/1999 | Brookhart et al. | |
| 5,880,323 A | 3/1999 | Brookhart et al. | |
| 6,245,871 B1 * | 6/2001 | Mackenzie et al. | ......... 526/141 |

FOREIGN PATENT DOCUMENTS

| | | |
|---|---|---|
| EP | 381495 | 1/1990 |
| EP | 748821 | 12/1996 |
| EP | 0 748 821 | 12/1996 |
| JP | 96-70332 | 9/1997 |
| JP | 96-84343 | 10/1997 |
| JP | 96-84344 | 10/1997 |
| WO | WO 96/23010 | 8/1996 |
| WO | WO9637522 | 11/1996 |
| WO | WO 9637523 | 11/1996 |
| WO | WO 97/02298 | 1/1997 |
| WO | WO 97/17380 | 5/1997 |
| WO | WO 97/38024 | 10/1997 |
| WO | WO 97/47661 | 12/1997 |
| WO | WO 97/48735 | 12/1997 |

(List continued on next page.)

OTHER PUBLICATIONS

L.K. Johnson, et al., J. Am. Chem. Soc., 1995, 117, No. 23, Jun. 14, 1995, 6414–6415.
G.F. Schmidt et al., J. Am. Chem. Soc. 1985, 107, 1443.
M. Brookhart et al. Macromolecules 1995, 28, 5378.
M. Peuckert et al., Organomet. 1983, 2 (5), 594.
W. Keim et al., Angew. Chem. Int. Ed. Eng. 1981, 20, 116.
V.M. Mohring et al., Angew. Chem. Int. Ed. Eng. 1985, 24, 1001.
G. Wilke, Angew. Chem. Int. Ed. Engl. 1988, 27, 185.
K.A.O. Starzewski et al., Angew. Chem. Int. Ed. Engl. 1987, 26, 63.
P. Wehman et al., Journal of Organometallic Chemistry, vol. 535, No. 1–2, May 15, 1997, 183–193.
E. Shirakawa et al., Tetrahedron Letters, vol. 38, No. 9, Jul. 21, 1997, 5177–5180.
Van Den Bueken et al., Chem. Commun. 1998, (2), 223–224.
Zhaozhong, Jiang et al., Macromolecules, (1994), 27(10), 2694–2700.
M. Hvastijova et al., Proc. Conf. Coord. Chem. (1987), 11$^{th}$, 109–114.

Primary Examiner—David W. Wu
Assistant Examiner—R. Rabago
(74) Attorney, Agent, or Firm—Kilpatrick Stockton LLP

(57) ABSTRACT

The present invention includes novel ligands which may be utilized as part of a catalyst system. A catalyst system of the present invention is a transition metal-ligand complex. In particular, the catalyst system includes a transition metal component and a ligand component comprising a Nitrogen atom and/or functional groups comprising a Nitrogen atom, generally in the form of an imine functional group. In certain embodiments, the ligand component may further comprise a phosphorous atom. Preferred ligand components are bidentate (bind to the transition metal at two or more sites) and include a nitrogen-transition metal bond. The transition metal-ligand complex is generally cationic and associated with a weakly coordinating anion. A catalyst system of the present invention may further comprise a Lewis or Bronsted acid. The Lewis or Bronsted acid may be complexed with the ligand component of the transition metal-ligand complex.,

20 Claims, No Drawings

FOREIGN PATENT DOCUMENTS

| | | |
|---|---|---|
| WO | WO 97/48736 | 12/1997 |
| WO | WO 97/48737 | 12/1997 |
| WO | WO 97/48742 | 12/1997 |
| WO | WO 98/03521 | 1/1998 |
| WO | WO 98/03559 | 1/1998 |
| WO | WO 9830610 | 7/1998 |
| WO | WO 98/30610 | 7/1998 |
| WO | WO 98/42440 | 10/1998 |
| WO | WO 9842664 | 10/1998 |
| WO | WO 9842665 | 10/1998 |
| WO | WO 9847934 | 10/1998 |
| WO | WO 98/49208 | * 11/1998 |
| WO | WO 9856832 | 12/1998 |
| WO | WO 9856837 | 12/1998 |
| WO | WO 9856839 | 12/1998 |
| WO | WO 9902472 | 1/1999 |
| WO | WO 9905189 | 2/1999 |
| WO | WO 9909078 | 2/1999 |

* cited by examiner

CATALYST COMPOSITIONS FOR THE POLYMERIZATION OF OLEFINS

CROSS REFERENCE TO RELATED APPLICATIONS

This is a divisional application of U.S. patent application Ser. No. 09/222,614 filed Dec. 29, 1998, now U.S. Pat. No. 6,200,925, which is a continuation in part application of U.S. Ser. No. 09/028,315, filed on Feb. 24, 1998, now abandoned, the disclosure of which is incorporated herein by reference, and claims the benefit of the following provisional applications under 35 USC §119: Provisional Application Ser. No. 60/040,754, filed Mar. 13, 1997; Provisional Application Ser. No. 60/044,691, filed Apr. 18, 1997; Provisional Application Ser. No. 60/045,337, filed May 1, 1997; Provisional Application Ser. No. 60/045,358, filed May 2, 1997; Provisional Application Ser. No 60/045,357, filed May 2, 1997; and Provisional Application Ser. No. 60/045,697, filed May 6, 1997.

FIELD OF THE INVENTION

The present invention relates to catalyst compositions for olefin polymerization and processes for preparing polyolefins utilizing the catalysts. More particularly, the present invention relates to catalyst compositions comprising ligand complexes comprising nitrogen, for example, heterocycle groups.

BACKGROUND OF THE INVENTION

Olefin polymers are used in a wide variety of products, from sheathing for wire and cable to film. Olefin polymers are used, for instance in injection or compression molding applications, in extruded film sheeting, as extrusion coatings on paper, for example photographic paper and digital recording paper, and the like. Improvements in catalysts have made it possible to better control polymerization processes, and, thus influence the properties of the bulk material. Increasingly, efforts are being made to tune the physical properties of plastics for lightness, strength, resistance to corrosion, permeability, optical properties, and the like for particular uses. Chain length, polymer branching and functionality have a significant impact on the physical properties of the polymer. Accordingly, novel catalysts are constantly being sought in attempts to obtain a catalytic process for polymerizing olefins which permits more efficient and better-controlled polymerization of olefins.

Conventional polyolefins are prepared by a variety of polymerization techniques, including homogeneous liquid phase, gas phase, and slurry polymerization. Certain transition metal catalysts, such as those based on titanium compounds (e.g. $TiCl_3$ or $TiCl_4$) in combination with organoaluminum cocatalysts, are used to make linear and linear low-density polyethylenes as well as poly-α-olefins such as polypropylene. These so-called "Ziegler-Natta" catalysts are quite sensitive to oxygen and are ineffective for the copolymerization of nonpolar and polar monomers Recent advances in non-Ziegler-Natta olefin polymerization catalysis include the following.

L. K. Johnson et al., WO Patent Application 96/23010, disclose the polymerization of olefins using cationic nickel, palladium, iron, and cobalt complexes containing diimine and bisoxazoline ligands. This document also describes the polymerization of ethylene, acyclic olefins, and/or selected cyclic olefins and optionally selected unsaturated acids or esters such as acrylic acid or alkyl acrylates to provide olefin homopolymers or copolymers.

European Patent Application Serial No. 381,495 describes the polymerization of olefins using palladium and nickel catalysts that contain selected bidentate phosphorous containing ligands.

L. K. Johnson et al., *J. Am. Chem. Soc.*, 1995, 117, 6414, describe the polymerization of olefins such as ethylene, propylene, and 1-hexene using cationic α-diimine-based nickel and palladium complexes These catalysts have been described to polymerize ethylene to high molecular weight branched polyethylene. In addition to ethylene, Pd complexes act as catalysts for the polymerization and copolymerization of olefins and methyl acrylate.

G. F. Schmidt et al., *J. Am. Chem. Soc.* 1985, 107,1443, describe a cobalt(III) cyclopentadienyl catalytic system having the structure $[C_5Me_5(L)CoCH_2CH_2\text{-}\mu\text{-}H]^+$, which provides for the "living" polymerization of ethylene.

M. Brookhart et al., *Macromolecules* 1995, 28, 5378, disclose using such "living" catalysts in the synthesis of end-functionalized polyethylene homopolymers.

U. Klabunde, U.S. Pat. Nos. 4,906,754, 4,716,205, 5,030,606, and 5,175,326, describes the conversion of ethylene to polyethylene using anionic phosphorous, oxygen donors ligated to Ni(II). The polymerization reactions were run between 25 and 100° C. with modest yields, producing linear polyethylene having a weight-average molecular weight ranging between 8K and 350 K. In addition, Klabunde describes the preparation of copolymers of ethylene and functional group containing monomers M. Peuckert et al., *Organomet.* 1983, 2(5), 594, disclose the oligomerization of ethylene using phosphine, carboxylate donors ligated to Ni(II), which showed modest catalytic activity (0.14 to 1.83 TO/s) The oligomerizations were carried out at 60 to 95° C. and 10 to 80 bar ethylene in toluene, to produce α-olefins.

R. E. Murray, U.S. Pat. Nos. 4,689,437 and 4,716,138, describes the oligomerization of ethylene using phosphine, sulfonate donors ligated to Ni(II). These complexes show catalyst activities approximately 15 times greater than those reported with phosphine, carboxylate analogs.

W. Keim et al., *Angew. Chem. Int. Ed. Eng.* 1981, 20,116, and V. M Mohring, et al., *Angew. Chem. Int. Ed. Eng.* 1985, 24,1001. disclose the o polymerization of ethylene and the oligomerization of α-olefins with aminobis(imino) phosphorane nickel catalysts; G. Wilke, *Angew. Chem. Int. Ed. Engl.* 1988, 27, 185, describes a nickel allyl phosphine complex for the polymerization of ethylene.

K. A. O. Starzewski et al., *Angew. Chem. Int. Ed. Engl.* 1987, 26, 63, and U.S. Pat. No. 4,691,036, describe a series of bis(ylide) nickel complexes, used to polymerize ethylene to provide high molecular weight linear polyethylene.

WO Patent Application 97/02298 discloses the polymerization of olefins using a variety of neutral N, O, P, or S donor ligands, in combination with a nickel(0) compound and an acid.

Brown et al., WO 97/17380, describes the use of Pd α-diimine catalysts for the polymerization of olefins including ethylene in the presence of air and moisture.

Fink et al., U.S. Pat. No. , 4,724,273, have described the polymerization of α-olefins using aminobis(imino) phosphorane nickel catalysts and the compositions of the resulting poly(α-olefins).

Recently Vaughan et al. WO 9748736, Denton et al. WO 9748742, and Sugimura et al. WO 9738024 have described the polymerization of ethylene using silica supported α-diimine nickel catalysts.

Recently Canich et al. WO 9748735, and Mecking (Germ. Offr. DE 19707236 A1 980827) described the use of mixed α-diimine catalysts with group IV transition metal catalysts for the polymerization of olefins.

Additional recent developments are described by Sugimura et al., in JP96-84344, JP96-84343, by Yorisue et al., in JP96-70332, McLain et al. WO 9803559, Weinberg et al. WO 9803521 and by Matsunaga et al. WO 9748737.

Notwithstanding these advances in non-Ziegler-Natta catalysis, there remains a need for efficient and effective Group 8–10 transition metal catalysts for effecting polymerization of olefins. In addition, there is a need for novel methods of polymerizing olefins employing such effective Group 8–10 transition metal catalysts. In particular, there remains a need for Group 8–10 transition metal olefin polymerization catalysts with both improved temperature stability and functional group compatibility. Further, there remains a need for a method of polymerizing olefins utilizing effective Group 8–10 transition metal catalysts in combination with a Lewis acid so as to obtain a catalyst that is more active and more selective.

SUMMARY OF THE INVENTION

The present invention includes novel ligands, which may be utilized as part of a catalyst system. A catalyst system of the present invention is a transition metal-ligand complex. In particular, the catalyst system is comprised of a transition metal component and a ligand component comprising a nitrogen atom, generally in the form of an imine or heterocycle group. Preferred ligand components are bidentate and include a nitrogen-transition metal bond. The transition metal-ligand complex is generally cationic and associated with a weakly coordinating anion.

A catalyst system of the present invention may further comprise a Lewis or Bronsted acid. The Lewis or Bronsted acid may be complexed with the transition metal component and/or the ligand component of thee transition metal-ligand complex.

In one aspect of the present invention, the transition metal component of the catalyst system is Group 8–10 transition metals. In another aspect, the catalyst system further comprises a Lewis or Bronsted acid and the transition metal component is Group 8–10 transition metals. Preferred transition metal components include iron (Fe), cobalt (Co), nickel (Ni) and palladium (Pd). The choice of a particular transition metal may be made in view of the end use of the catalyst system.

The present invention provides a batch or continuous process for the polymerization of olefins, comprising contacting one or more monomers selected from compounds of the formula RCH=CHR$^1$ with a Group 8–10 transition metal complex of a ligand of the formula VI, XII, IX, XIII, XIV, XV, or XXII and optionally a Bronsted or Lewis acid,

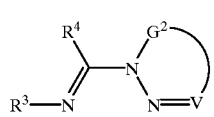

VI

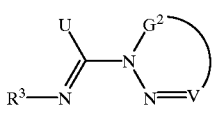

XII

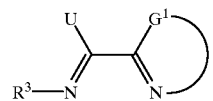

IX

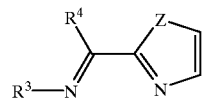

XIII

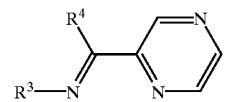

XIV

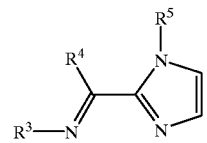

XV

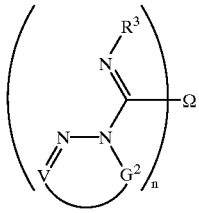

XXII wherein R and R$^1$ are independently H, hydrocarbyl, fluoroalkyl, or R and R$^1$ may be linked to form a cyclic olefin;

R$^3$ is hydrocarbyl or substituted hydrocarbyl;

R$^4$ is H, hydrocarbyl, substituted hydrocarbyl, or silyl;

R$^5$ is hydrocarbyl or substituted hydrocarbyl;

Z is O or S;

U is —OR$^{10}$, —SR$^{10}$, —SeR$^{10}$ or —NR$^{10}$R$^8$ wherein R$^{10}$ and R$^8$ are each independently selected from H, hydrocarbyl, substituted hydrocarbyl, or silyl, and in addition R$^{10}$ and R$^8$ may collectively form a ring with nitrogen.

G$^1$ is hydrocarbyl or substituted hydrocarbyl and may comprise a carbocyclic or heterocyclic ring, thereby forming a 5-membered or 6-membered heterocyclic ring comprising G$^1$, C, and N;

G$^2$ is hydrocarbyl or substituted hydrocarbyl and may comprise a carbocyclic or heterocyclic ring, thereby forming a 5-membered or 6-membered heterocyclic ring comprising G$^2$, V, N, and N;

V is —CR$^6$, N, or —PR$^6$R$^9$; wherein, R$^6$ and R$^9$ are each independently selected from H, hydrocarbyl, substituted hydrocarbyl, silyl or heteroatom connected hydrocarbyl, and in addition, R$^6$ and R$^9$ may collectively form a ring with phosphorus;

Ω is hydrocarbyl or substituted hydrocarbyl; and, n is an integer between 2 and 6.

The present invention also provides novel catalysts useful for the polymerization of olefins comprising (a) a Group 8–10 transition metal, (b) a ligand of the formula VI, XII, IX, XIII, XIV, XV, or XXII and optionally (c) a Bronsted or Lewis acid,

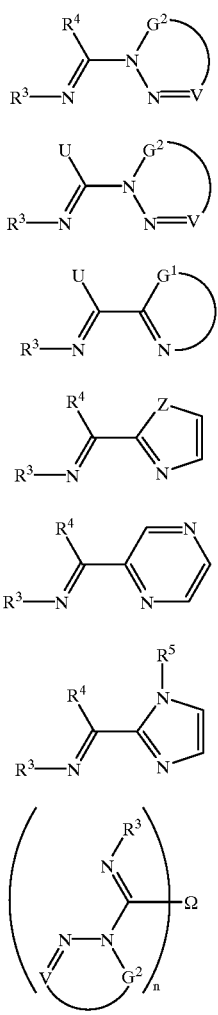

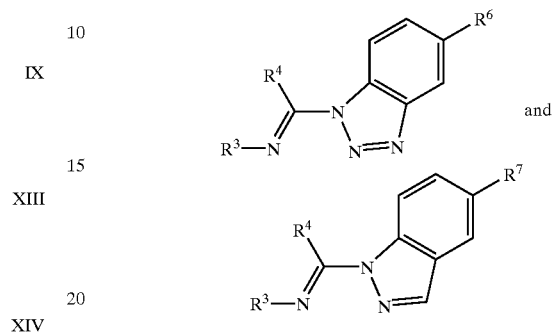

wherein R³ is hydrocarbyl or substituted hydrocarbyl;
R⁴ is H, hydrocarbyl, substituted hydrocarbyl, or silyl,
R⁵ is hydrocarbyl or substituted hydrocarbyl;
Z is O or S;
U is —OR¹⁰, —SR¹⁰, —SeR¹⁰ or —NR¹⁰R⁸, wherein R¹⁰ and R⁸ are each independently selected from H, hydrocarbyl, substituted hydrocarbyl, or silyl, and in addition R¹⁰ and R⁸ may collectively form a ring with nitrogen,
G¹ is hydrocarbyl or substituted hydrocarbyl and may comprise a carbocyclic or heterocyclic ring, thereby forming a 5-membered or 6-membered heterocyclic ring comprising G¹, C, and N;
G² is hydrocarbyl or substituted hydrocarbyl and may comprise a carbocyclic or heterocyclic ring, thereby forming a 5-membered or 6-membered heterocyclic ring comprising G², V, N, and N;
V is —CR⁶, N, or —PR⁶R⁹; wherein, R⁶ and R⁹ are each independently selected from H, hydrocarbyl, substituted hydrocarbyl, silyl or heteroatom connected hydrocarbyl, and in addition, R⁶ and R⁹ may collectively form a ring with phosphorus;
Ω is hydrocarbyl or substituted hydrocarbyl; and,
n is an integer between 2 and 6.

In the above process, it should be appreciated that the Group 8–10 transition metal has coordinated thereto a ligand having the formula VII, XII, IX, XIII, XIV, or XXII, and that component (c) is optionally reacted with this metal-ligand complex Preferred catalysts are those wherein the ligand of formula VI is selected from:

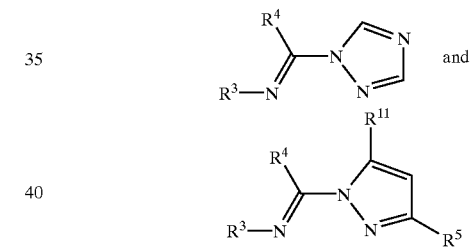

wherein R³ is hydrocarbyl or substituted hydrocarbyl;

R⁴ is H, hydrocarbyl, substituted hydrocarbyl, or silyl;

R⁵, R⁶ and R¹¹ are independently H, hydrocarbyl, or substituted hydrocarbyl;

R⁷ is H, hydrocarbyl, substituted hydrocarbyl, or NO₂. In a further preferred embodiment, the ligand of formula VI is selected from

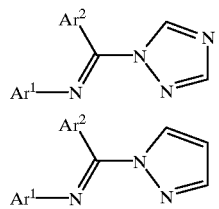

wherein R³ is hydrocarbyl or substituted hydrocarbyl,

R⁴ is H, hydrocarbyl, substituted hydrocarbyl, or silyl; and.

R⁵ and R¹¹ are independently H, hydrocarbyl, or substituted hydrocarbyl. Further preferred ligands of formula VI include wherein Ar¹ is 2,6-dimethylphenyl or 2,6-diisopropylphenyl: and.

Ar² is phenyl or 1-naphthyl.

Preferred ligands of the formula XII include

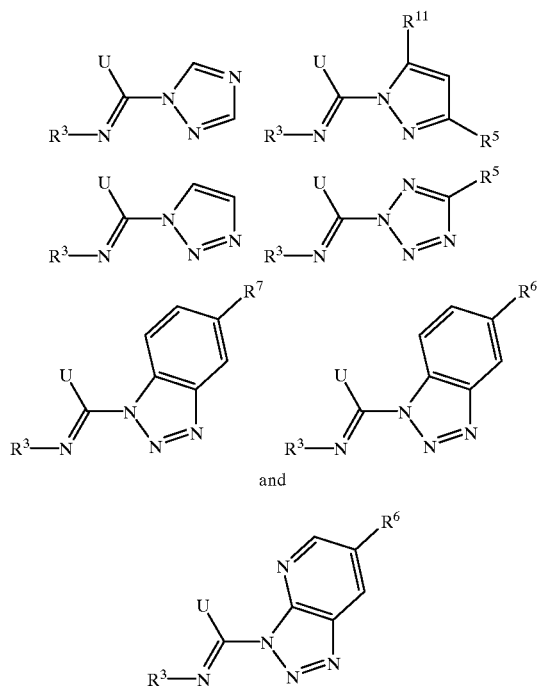

and wherein $R^3$, $R^5$, $R^6$, $R^7$, $R^{11}$ and U are defined as above.

The catalyst system of this invention is extremely versatile in that changes in the ligand or changes to the transition metal itself can be made to obtain a "tailor made" catalyst to suit a particular set of requirements for a particular monomer and polymer. Also, the catalyst of the present invention may be used under a variety of reaction conditions including temperatures between about −100 and 200° C. and pressures between about 1 and 100 atmospheres. Additionally, the catalysts of the present invention may be used in solution, slurry or gas phase polymerizations. Further, the catalysts may be attached to a solid support. In certain embodiments of the present invention, a Lewis or Bronsted acid may be used as a co-catalyst to render the transition metal more electron deficient, and therefore more active and/or selective, and/or act as a site to bind the catalyst to a surface.

Further features and advantages of the catalyst system and processes of the present invention will become more apparent from the following more detailed description.

DETAILED DESCRIPTION OF THE INVENTION

The novel ligand components of the present invention are broadly described as comprising a nitrogen atom, preferably in the form of an imine or heterocyclic functional group.

A catalyst system of the present invention may further comprise a Lewis or Bronsted acid, which may be complexed with the ligand component or the transition metal component. While not wishing to be bound by theory, it is believed that the Lewis acid complexation can render the transition metal more electron deficient, and therefore more active and/or selective, and/or act as a site to bind the catalyst to a surface. Although this strategy may be implemented in a variety of ways, ligands in which the Lewis acid is bound to one or more heteroatoms which are π-conjugated to the donor atom or atoms bound to the transition metal are preferred.

In one aspect of the present invention, the transition metal component of the catalyst system is a Group 8–10 transition metal. In another aspect, the catalyst system further is a Lewis or Bronsted acid and the transition metal component is a Group 8–10 transition metal. A catalyst system of the present invention may advantageously be utilized in a process for the polymerization of olefins including ethylene and α-olefins such as propylene and 1-hexene and cyclic olefins such as cyclopentene and norbornene. Accordingly, a process of the present invention is contacting one or more monomers comprising $RCH=CHR^1$ with a catalyst system of the present invention at a temperature and a pressure sufficient to effect polymerization, preferably a temperature of −100 to 200° C., more preferably a temperature from 25 to 150° C., and a pressure of from about 1 atmosphere to 100 atmospheres, wherein R and $R^1$ are independently hydrogen, hydrocarbyl, fluoroalkyl, or R and $R^1$ may be linked to form a cyclic olefin. The possible embodiments of a process of the present invention for the production of polyolefins include processes utilizing the catalyst systems of the present invention described herein.

The embodiments of a catalyst system of the present invention are described in detail below utilizing the following terms defined as follows:

Symbols ordinarily used to denote elements in the Periodic Table take their ordinary meaning, unless otherwise specified. Thus, N, O, S, P, and Si stand for nitrogen, oxygen, sulfur, phosphorus and silicon, respectively.

Examples of neutral Lewis bases include, but are not limited to, organic ethers, organic nitrites or organic sulfides.

Examples of Lewis acids include, but are not limited to, methylaluminoxane (hereinafter MAO) and other aluminum sesquioxides, $R^7_3Al$, $R^7_2AlCl$, $R^7AlCl_2$ (where $R^7$ is alkyl), organoboron compounds, boron halides, $B(C_6F_5)_3$, $R^9_3Sn[BF_4]$, (where $R^9$ is alkyl or aryl), $MgCl_2$, and $H^+X^-$, where $X^-$ is a weakly coordinating anion.

A "hydrocarbyl" group means a monovalent or divalent, linear, branched or cyclic group which contains only carbon and hydrogen atoms Examples of monovalent hydrocarbyls include the following: $C_1$–$C_{20}$ alkyl: $C_1$–$C_{20}$ alkyl substituted with one or more groups selected from $C_1$–$C_{20}$ alkyl. $C_3$–$C_8$ cycloalkyl or aryl; $C_3$–$C_8$ cycloalkyl, $C_3$–$C_8$ cycloalkyl substituted with one or more groups selected from $C_1$–$C_{20}$ alkyl, $C_3$–$C_8$ cycloalkyl or aryl, $C_5$–$C_{14}$ aryl; and $C_6$–$C_{14}$ aryl substituted with one or more groups selected from $C_1$–$C_{20}$ alkyl, $C_3$–$C_8$ cycloalkyl or aryl. As used herein, the term "aryl" preferably denotes a phenyl, napthyl, or anthracenyl group. When the above groups are substituted, they are preferably substituted from one to four times with the listed groups. Examples of divalent (bridging hydrocarbyls) include: —$CH_2$—, —$CH_2CH_2$—, —$C_6H_4$—, and —$CH_2CH_2CH_2$—.

Specific examples of $G^2$ as used herein include, but are not limited to: —$CH_2$—$CH_2$—, —$CH_2$—O—, —$N(CH_3)$—$CH_2$—, —$CH_2$—$CH_2$—O—, —$N(CH_3)$—$CH_2$—$CH_2$—, —S—$CH_2$—, —S—$CH_2$—$CH_2$—, —CH=CH—, —CH=N—, —CH=CH—$CH_2$—, —CH=N—$CH_2$—, and —$C_6H_4$—.

A "silyl" group refers to a $SiR_3$ group where Si is silicon and R is hydrocarbyl or substituted hydrocarbyl or silyl, as in $Si(SiR_3)_3$ A "heteroatom" refers to an atom other than carbon or hydrogen. Preferred heteroatoms include oxygen, nitrogen, phosphorus, sulfur, selenium, arsenic, chlorine, bromine, and fluorine.

The term "fluoroalkyl" as used herein refers to a $C_1$–$C_{20}$ alkyl group substituted with one or more fluorine atoms.

A "substituted hydrocarbyl" refers to a monovalent or divalent hydrocarbyl substituted with one or more heteroatoms. Examples of monovalent substituted hydrocarbyls include: trifluoromethyl, 2,6-dimethyl-4-methoxyphenyl, 2,6-diisopropyl-4-methoxyphenyl, 4-cyano-2,6-dimethylphenyl, 2,6-dimethyl-4-nitrophenyl, 2,6-difluorophenyl, 2,6-dibromophenyl, 2,6-dichlorophenyl, 4-methoxycarbonyl-2,6-dimethylphenyl, 2-tert-butyl6-chlorophenyl, 2,6-dimethyl-4-phenylsulfonylphenyl, 2,6-dimethyl-4-nitrophenyl, 2,6-dimethyl4-trifluoromethylphenyl, 2,6-dimethyl-4-trimethylammoniumphenyl (associated with a weakly coordinating anion), 2,6-dimethyl-4-hydroxyphenyl, 9-hydroxyanthr-10-yl, 2-chloronapth-1-yl, 4-methoxyphenyl, 4-nitrophenyl, and 9-nitroanthr-10-yl. Examples of divalent substituted hydrocarbyls include 4-methoxy-1,2-phenylene, 1-methoxymethyl-1,2-ethanediyl, 1,2-bis(benzyloxymethyl)-1,2-ethanediyl, and 1-(4-methoxyphenyl)-1,2-ethanediyl.

A "mono-olefin" means a hydrocarbyl group having one carbon-carbon double bond.

The term "polymer" as used herein is meant a species comprised of monomer units and having a degree of polymerization (DP) of ten or higher.

The term "weakly coordinating anion" is well-known in the art per se and generally refers to a large bulky anion capable of delocalization of the negative charge of the anion. Suitable weakly coordinating anions include, but are not limited to, $PF_6^-$, $BF_4^-$, $SbF_6^-$, $(Ph)_4B^-$ where Ph=phenyl, $^{-BAr}\!_4$ where $^{-BAr}\!_4$=tetrakis[3,5-bis(trifluoromethyl)phenyl] borate. The coordinating ability of such anions is known and described in the literature (Strauss, S. et al, *Chem. Rev.* 1993, 93, 927).

As used herein, the terms "monomer" or "olefin monomer" refer to the olefin or other monomer compound before it has been polymerized. The term "monomer units" refers to the moieties of a polymer that correspond to the monomers after they have been polymerized.

In some cases, a compound Y is required as a cocatalyst. Suitable compounds Y include a neutral Lewis acid capable of abstracting Q⁻ or W⁻ (as defined below) to form a weakly coordinating anion, a cationic Lewis acid whose counterion is a weakly coordinating anion, or a Bronsted acid whose conjugate base is a weakly coordinating anion. Preferred compounds Y include: methylaluminoxane (hereinafter MAO) and other aluminum sesquioxides, $R^7{}_3Al$, $R^7{}_2AlCl$, $R^7AlCl_2$ (where $R^7$ is alkyl), organoboron compounds, boron halides, $B(C_6F_5)_3$, $R^9{}_3Sn[BF_4]$, (where $R^9$ is alkyl or aryl), $MgCl_2$, and $H^+X^-$, where X is a weakly coordinating anion.

Examples of "solid support" include inorganic oxide support materials, such as: talcs, silicas, titania, silica/chromia, silica/chromia/titania, silica/alumina, zirconia, aluminum phosphate gels silanized silica, silica hydrogels, silica xerogels: silica aerogels. montmorillonite clay and silica co-gels as well as organic solid supports such as polystyrene and functionalized polystyrene (See, for example, Roscoe, S. B.; Frechet, J. M. J.; Walzer, J. F.; Dias, A. J.; "Polyolefin Spheres from Metallocenes Supported on Non-interacting Polystyrene", 1998, Science, 280, 270–273 (1998).) An especially preferred solid support is one which has been pre-treated with Y compounds as described herein, most preferably with MAO. Thus, in a preferred embodiment, the catalysts of the present invention are attached to a solid support (by "attached to a solid support" is meant ion paired with a component on the surface, adsorbed to the surface or covalently attached to the surface) which has been pre-treated with a compound Y. Alternatively, the catalyst, the compound Y, and the solid support can be combined in any order, and any number of Y compounds can be utilized; in addition, the supported catalyst thus formed may be treated with additional quantities of compound(s) Y. In an especially preferred embodiment, the compounds of the present invention are attached to silica which has been pre-treated with MAO. Such supported catalysts are prepared by contacting the transition metal compound, in a substantially inert solvent—by which is meant a solvent which is either unreactive under the conditions of catalyst preparation, or if reactive, acts to usefully modify the catalyst activity or selectivity—with MAO treated silica for a sufficient period of time to generate the supported catalysts. Examples of substantially inert solvents include toluene mineral spirits, hexane, $CH_2Cl_2$ and $CHCl_3$.

Preferred polyolefin products will have a degree of polymerization (DP) of at least 10. A preferred olefin monomer is $RCH=CHR^1$ wherein R and RI are independently H, hydrocarbyl, fluoroalkyl, or R and $R^1$ may be linked to form a cyclic olefin. Especially preferred olefin monomers include ethylene, propylene, 1-butene, 1-pentene, 1-hexene. 1-heptene cyclopentene, and norbornene.

The preferred temperature range for the polymerization reaction is about −100 to 200° C., more preferably a temperature from about 25 to 150° C.; a preferred pressure is about 1 atmosphere to 100 atmospheres.

The present invention provides a catalyst system comprising a transition metal complex of bidentate ligands having a five-membered ring, formed by the metal complex, and preferably comprising one metal atom, one carbon atom, and three nitrogen atoms.

The olefin polymerization catalysts of the present invention comprise transition metal complexes of bidentate ligands that can be referred to as imino-substituted heterocycles, more specifically imino-substituted pyrazoles, triazoles and other related heterocycles. The transition metal component is a Group 8–10 transition metal. Nickel, cobalt and palladium are preferred transition metals. The ligands may also be referred to using a "imine/heterocycle" or "heterocycle/imine" nomenclature, which describes the two components of the bidentate ligand, e.g., imine/triazole. The five-membered ring formed by the transition metal complex preferably contains one transition metal atom, one carbon atom, and three nitrogen atoms (two of which are provided by the heterocycle component of the bidentate ligand).

While not wishing to be bound by theory, the inventors believe that the active catalytic specie of the present invention is a transition metal complex of the formula I

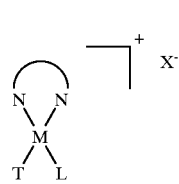

I wherein M is Group 8–10 transition metal, preferably Ni, Pd, Fe or Co;

T is H, or hydrocarbyl;

L is a mono-olefin, or a neutral lewis base wherein the coordinated atom is nitrogen, oxygen, or sulfur;

X⁻ is a weakly coordinating anion; and,

is a bidentate N,N donor imine/heterocycle ligand selected from ligands of the formula VI, XII, IX, XIII, XIV, XV, and XXII:

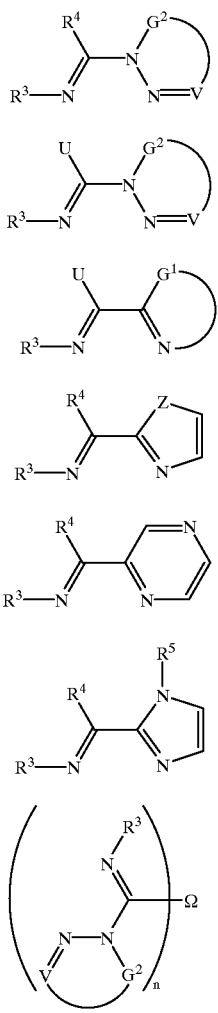

wherein R³ is hydrocarbyl or substituted hydrocarbyl;
R⁴ is H, hydrocarbyl, substituted hydrocarbyl or silyl:
R⁵ is hydrocarbyl or substituted hydrocarbyl;
Z is O or S;
U is —OR¹⁰, —SR¹⁰, —SeR¹⁰ or —NR¹⁰R⁸, wherein R¹⁰ and R⁸ are each independently selected from H, hydrocarbyl, substituted hydrocarbyl, or silyl, and in addition R¹⁰ and R⁸ may collectively form a ring with nitrogen;
G¹ is hydrocarbyl or substituted hydrocarbyl and may comprise a carbocyclic or heterocyclic ring, thereby forming a 5-membered or 6-membered heterocyclic ring comprising G¹, C, and N;
G² is hydrocarbyl or substituted hydrocarbyl and may comprise a carbocyclic or heterocyclic ring, thereby forming a 5-membered or 6-membered heterocyclic ring comprising G², V, N, and N;

V is —CR⁶, N, or —PR⁶R⁹; wherein, R⁶ and R⁰ are each independently selected from H, hydrocarbyl, substituted hydrocarbyl, silyl or heteroatom connected hydrocarbyl, and in addition, R⁶ and R⁹ may collectively form a ring with phosphorus;
Ω is hydrocarbyl or substituted hydrocarbyl; and,
n is an integer between 2 and 6.

Preferred catalysts of formula I are those which comprise a ligand of the formula VI or XXII.

Thus, in the case of a ligand of formula VI, the present invention provides a catalyst system comprising a transition metal-ligand complex of the formula IV:

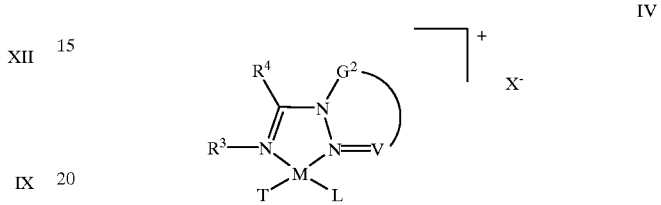

wherein:
R³ is hydrocarbyl or substituted hydrocarbyl;
R⁴ is hydrogen, hydrocarbyl, substituted hydrocarbyl, or silyl;
G² is hydrocarbyl or substituted hydrocarbyl and may comprise a carbocyclic or heterocyclic ring, thereby forming a 5-membered or 6-membered heterocyclic ring comprising G², V, N, and N;
V is CR⁶, N, or PR⁶R⁹;
R⁶ and R⁹ are each independently selected from hydrogen, hydrocarbyl, substituted hydrocarbyl, silyl or heteroatom connected hydrocarbyl, and in addition, R⁶ and R⁹ may collectively form a ring with phosphorus;
T is hydrogen, hydrocarbyl, or substituted hydrocarbyl
L is a monoolefin or a neutral Lewis base where the donating atom is nitrogen, oxygen, sulfur;
M is Ni(II), Pd(II), or Co(II); and
X⁻ is a weakly coordinating anion.

Further, with regard to active species utilizing ligands of the formula XXII, the present invention provides a catalyst system comprising a transition metal-ligand complex of the formula XXIII:

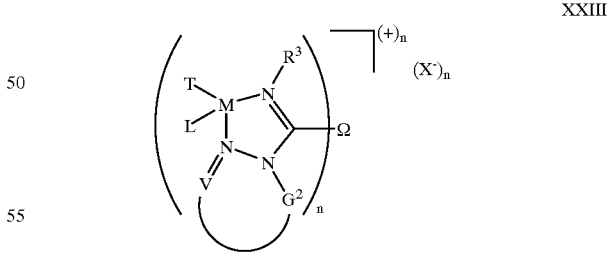

wherein:
R³ is hydrocarbyl or substituted hydrocarbyl;
G² is hydrocarbyl or substituted hydrocarbyl and may comprise a carbocyclic or heterocyclic ring, thereby forming a 5-membered or 6-membered heterocyclic ring comprising G², V, N, and N;
V is CR⁶, N, or PR6R⁹;
R⁶ and R⁹ are each independently selected from hydrogen. hydrocarbyl, substituted hydrocarbyl, silyl or heteroatom connected hydrocarbyl, and in addition, $R^6$ and $R^9$ may collectively form a ring with phosphorus;

$\Omega$ is hydrocarbyl or substituted hydrocarbyl;

n is an integer between 2 and 6;

T is hydrogen, hydrocarbyl, or substituted hydrocarbyl:

L is a monoolefin or a neutral Lewis base where the donating atom is nitrogen, oxygen, sulfur;

M is Ni(II), Pd(II), or Co(II); and $X^-$ is a weakly coordinating anion.

Preferred ligands of formula VI include the following:

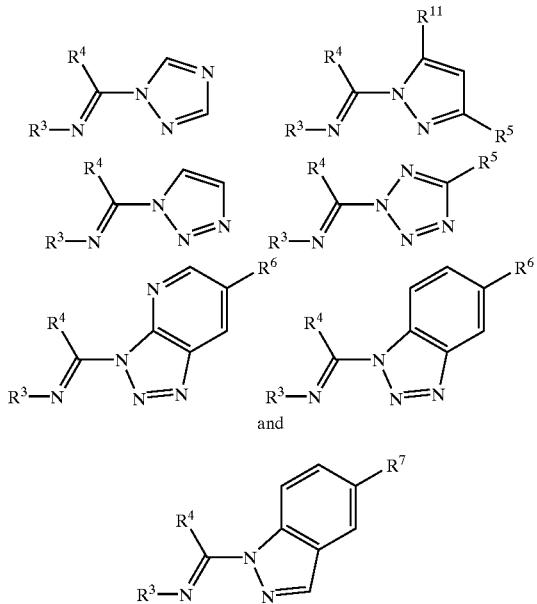

wherein $R^3$ is hydrocarbyl or substituted hydrocarbyl;

$R^4$ is H, hydrocarbyl, substituted hydrocarbyl, or silyl;

$R^5$, $R^6$ and $R^{11}$ are independently H, hydrocarbyl, or substituted hydrocarbyl;

$R^7$ is H, hydrocarbyl, substituted hydrocarbyl, or $NO_2$.

Further preferred ligands of formula VI include

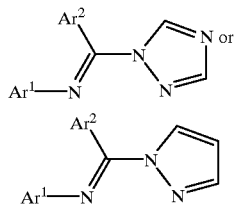

wherein $Ar^1$ is 2,6-dimethylphenyl or 2,6-diisopropylphenyl; and, $Ar^2$ is phenyl or 1-naphthyl.

Preferred ligands of formula XII include the following:

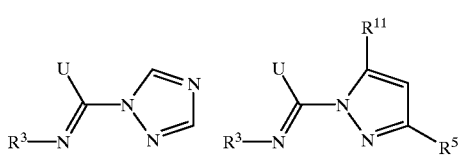

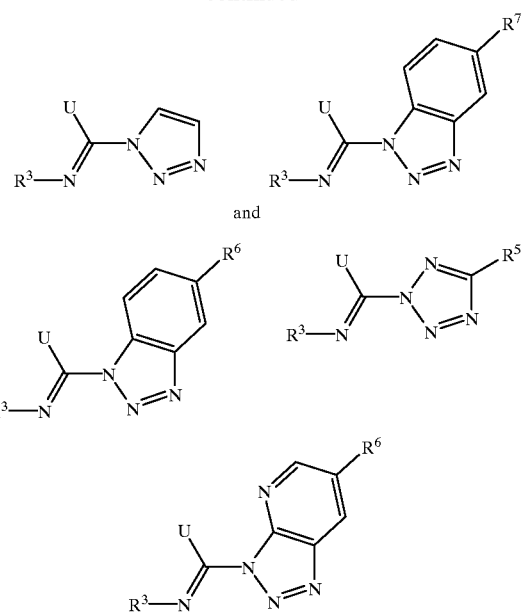

wherein $R^3$ is hydrocarbyl or substituted hydrocarbyl;

U is $-OR^{10}$, $-SR^{10}$, $-SeR^{10}$ or $-NR^{10}R^8$, wherein $R^{10}$ and $R^8$ are each independently selected from H, hydrocarbyl, substituted hydrocarbyl, or silyl, and in addition $R^{10}$ and $R^6$ may collectively form a ring with nitrogen;

$R^5$, $R^6$ and $R^{11}$ are independently H, hydrocarbyl, or substituted hydrocarbyl;

$R^7$ is H, hydrocarbyl, substituted hydrocarbyl, or $NO_2$.

Further preferred ligands of formula XII include:

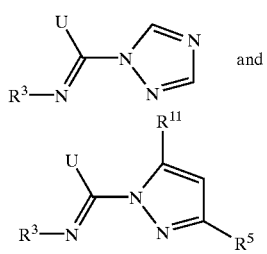

Preferred ligands of formula IX include

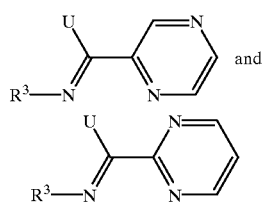

wherein $R^3$ is hydrocarbyl or substituted hydrocarbyl;

$R^{11}$ is hydrocarbyl, or substituted hydrocarbyl;

U is $OR^{10}$, $SR^{10}$, $SeR^{10}$ or $NR^{10}R^8$, wherein $R^{10}$ and $R^8$ are each independently selected from H, hydrocarbyl, substituted hydrocarbyl or silyl and in addition $R^{10}$ and $R^8$ may collectively form a ring with nitrogen and Z is oxygen or sulfur.

In formula XXII, preferred Ω groups include the following:

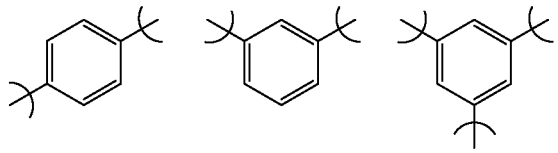
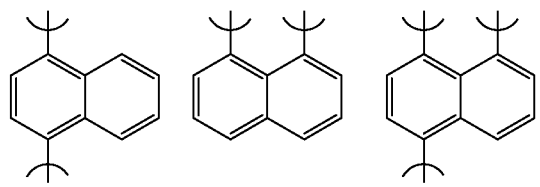
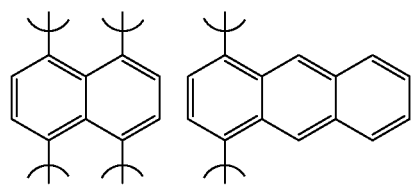
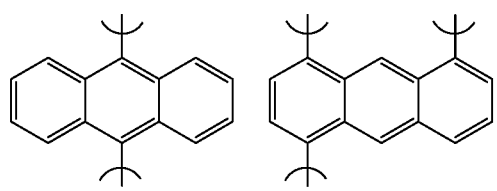
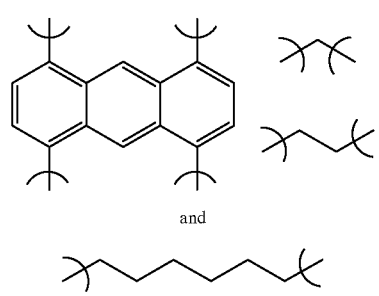

and

We recognize that there are numerous methodologies available to prepare the catalytically active complex of formula I. The methodologies include reacting a catalyst precursor complex of formula II (described below) with a Lewis acid (such as methylaluminoxane) in the presence of a mono-olefin (such as ethylene) to generate in situ a catalytically active specie of formula I. The catalyst precursor complex of formula II has a formula of:

II

wherein M is Group 8–10 transition metal, preferably Ni, Pd. Fe or Co;

Q is hydrocarbyl, chloride, iodide, or bromide,

W is hydrocarbyl, chloride, iodide, or bromide; and,

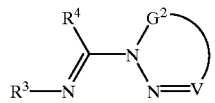

is a bidentate N,N donor imine/heterocycle ligand selected from ligands of the formula VI, XII, IX, XIII, XIV, XV, and XXII wherein $R^3$ is hydrocarbyl or substituted hydrocarbyl;

VI

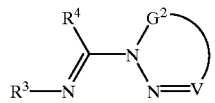

XII

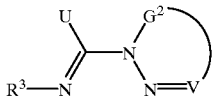

IX

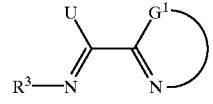

XIII

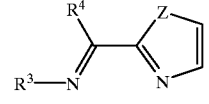

XIV

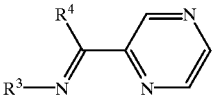

XV

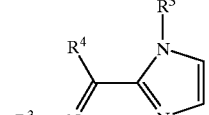

XXII

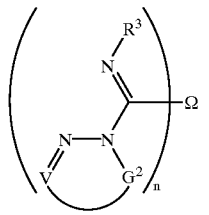

$R^4$ is H, hydrocarbyl, substituted hydrocarbyl, or silyl;
$R^5$ is hydrocarbyl or substituted hydrocarbyl;
Z is O or S;
U is $-OR^{10}$, $-SR^{10}$, $-SeR^{10}$ or $-NR^{10}R^8$, wherein $R^{10}$ and $R^8$ are each independently selected from H, hydrocarbyl, substituted hydrocarbyl, or silyl, and in addition $R^{10}$ and $R^8$ may collectively form a ring with nitrogen:
$G^1$ is hydrocarbyl or substituted hydrocarbyl and may comprise a carbocyclic or heterocyclic ring, thereby forming a 5-membered or 6-membered heterocyclic ring comprising $G^1$, C, and N;
$G^2$ is hydrocarbyl or substituted hydrocarbyl and may comprise a carbocyclic or heterocyclic ring, thereby forming a 5-membered or 6-membered heterocyclic ring comprising $G^2$, V, N, and N;

V is $CR^6$, N, or $PR^6R^9$; wherein, $R^6$ and $R^9$ are each independently selected from H, hydrocarbyl, substituted hydrocarbyl, silyl or heteroatom connected hydrocarbyl, and in addition, $R^6$ and $R^9$ may collectively form a ring with phosphorus;

Ω is hydrocarbyl or substituted hydrocarbyl; and, n is an integer between 2 and 6. Specific examples of this methodology are detailed in the example section below.

Preferred catalysts of formula II are those which comprise a ligand of the formula VI or XXII.

Thus, in the case of a ligand of formula VI, the present invention provides a catalyst system formed by contacting a first compound Y with a second compound V having the formula:

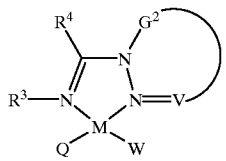

V wherein:

$R^3$ is hydrocarbyl or substituted hydrocarbyl;

$R^4$ is hydrogen, hydrocarbyl, substituted hydrocarbyl, or silyl;

$G^2$ is hydrocarbyl or substituted hydrocarbyl and may comprise a carbocyclic or heterocyclic ring, thereby forming a 5-membered or 6-membered heterocyclic ring comprising $G^2$, V, N, and N;

V is $CR^6$, N, or $PR^6R^9$;

$R^6$ and $R^9$ are each independently selected from hydrogen, hydrocarbyl, substituted hydrocarbyl, silyl or heteroatom connected hydrocarbyl, and in addition, $R^6$ and $R^9$ may collectively form a ring with phosphorus;

Q is hydrocarbyl, chloride, iodide, or bromide,

W is hydrocarbyl, chloride, iodide, or bromide;

M is Ni(II), Pd(II), or Co(II);

and Y is selected from a neutral Lewis acid capable of abstracting Q⁻ or W⁻ to form a weakly coordinating anion, a cationic Lewis acid whose counterion is a weakly coordinating anion, or a Bronsted acid whose conjugate base is a weakly coordinating anion.

Further, with regard to active species utilizing ligands of the formula XXII, the present invention provides a catalyst system formed by contacting a first compound Y with a second compound XXIV having the formula:

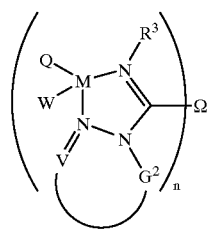

XXIV wherein:

R3 is hydrocarbyl or substituted hydrocarbyl;

$G^2$ is hydrocarbyl or substituted hydrocarbyl and may comprise a carbocyclic or heterocyclic ring, thereby forming a 5-membered or 6-membered heterocyclic ring comprising $G^2$, V, N, and N;

V is $CR^6$, N, or $PR^6R^9$;

$R^6$ and $R^9$ are each independently selected from hydrogen, hydrocarbyl, substituted hydrocarbyl, silyl or heteroatom connected hydrocarbyl, and in addition, $R^6$ and $R^9$ may collectively form a ring with phosphorus;

Q is hydrocarbyl, chloride, iodide, or bromide;

W is hydrocarbyl, chloride, iodide, or bromide;

M is Ni(II), Pd(II), or Co(II); Ω is hydrocarbyl or substituted hydrocarbyl n is an integer between 2 and 6:

and Y is selected from a neutral Lewis acid capable of abstracting Q⁻ or W⁻ to form a weakly coordinating anion, a cationic Lewis acid whose counterion is a weakly coordinating anion, or a Bronsted acid whose conjugate base is a weakly coordinating anion.

Preferred neutral Lewis acids include: MAO and other aluminum sesquioxides, $R_3^7Al$, $R^7_2AlCl$, and $R^7AlCl_2$ wherein $R^7$ is alkyl. Complex V and compound Y may be combined in the liquid phase. The liquid phase may include solvent or neat monomer. In a process for preparing polyolefins, complex V and compound Y may be combined in the presence of monomer The molar ratio of compound Y to complex V may be from about 10 to 10,000.

A second methodology for the in situ generation of an active complex of the formula I involves contacting a ligand with a suitable transition metal complex in the presence of a Bronsted acid and ethylene to provide an active catalyst. An example of using this methodology to prepare a catalyst of formula I would involve contacting a ligand of formula VI, XII, IX, XIII, XIV, XV, or XXII (as described above) with a suitable Ni complex (such as $Ni(1,5-cyclooctadiene)_2$) and a Bronsted acid (such as $HB(Ar)_4$ where Ar is 3,5-bis(trifluoromethyl)phenyl) in the presence of an olefin (such as ethylene) to generate an active olefin polymerization catalyst of formula I. Specific examples of this methodology are detailed in the example section below. (See also, L. K. Johnson et al., WO Patent Application 96/23010).

Preferred neutral Lewis acids include: MAO and other aluminum sesquioxides, $R_3^7Al$, $R^7_2AlCl$, and $R^7AlCl_2$ wherein $R^7$ is alkyl.

The skilled artisan, in possession of this disclosure, could make the present compounds without undue experimentation. Methods of synthesizing complexes I and II and compounds VI, XII, IX, XIII, XIV, XV, and XXII are also illustrated in the following examples.

Preferred ligand components for use in complex I or II and preferred catalyst systems utilizing complex I or II are also set forth in the following examples.

The present invention also provides processes for preparing polyolefins utilizing complexes I, II, and compounds VI, XII, IX, XII, XIV, XV, and XXII.

The present invention also provides a class of olefin polymerization catalysts based on late transition metal complexes of bidentate ligands comprising one imidate ester, thioimidate ester, selenoimidate ester, or amidine N-donor fragment, and one heterocyclic N-donor fragment, the two fragments together comprising a neutral bidentate, N,N-donor ligand. In one aspect, the catalyst "system" further comprises a Lewis or Bronsted acid.

An electron deficient metal center is advantageous for efficient olefin polymerization. A further embodiment of the present invention provides catalyst systems wherein a binucleating or multinucleating ligand is complexed to a transition metal and one or more Lewis acids to obtain an active olefin polymerization catalyst. While not wishing to be bound by any theory, it is believed that the Lewis acid complexation renders the transition metal more electron deficient rendering the transition metal catalyst more active and/or selective, and/or potentially providing a site to bind the catalyst system to a surface. Thus, broadly, catalyst systems of this embodiment of the present invention comprise ligand components, such as the ligand components described above, complexed with a transition metal and a Lewis acid. Preferred catalyst systems of this embodiment of the present invention include catalyst systems wherein the Lewis acid is bound to one or more heteroatoms which are π-conjugated to the donor atom or atoms bound to the transition metal.

Thus, in a further preferred embodiment, the invention provides a process for the polymerization of olefins comprising contacting one or more monomers of the formula RCH=CHR$^1$ with a binucleating or multinucleating ligand complexed to a Group 8–10 transition metal M and one or more Lewis acids, wherein the Lewis acid or acids are bound to one or more heteroatoms which are π-conjugated to the donor atom or atoms bound to the transition metal M; and R and R$^1$ are each, independently selected from hydrogen, hydrocarbyl, fluoroalkyl, or may be linked to form a cyclic olefin.

Examples of catalyst systems comprising a Lewis acid-ligand-transition metal complex of the present invention include XIX:

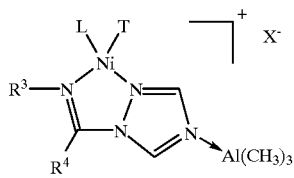

XIX wherein

R$^3$, R$^4$, L, and T are defined as above.

Complex XIX may be produced by synthesizing the transition metal-ligand complex in the manner described above and exemplified in the example herein, and then combining the transition metal-ligand complex with the Lewis acid component.

The present invention also describes a process for preparing polyolefins comprising contacting one or more olefin monomers with a catalyst system at a temperature and a pressure sufficient to effect polymerization, wherein the catalyst system comprises a transition metal-ligand-Lewis acid complex, e.g. complex XIX of the above embodiment of the present invention.

As noted above, it is preferred that certain of the compounds of the present invention be attached to a solid support which has been pre-treated with a compound Y, for example, MAO, or mixed with Y in any order When such supported catalysts are used in slurry and gas phase ethylene polymerizations, novel polymer compositions are provided insofar as such compositions are blends of different polyolefin polymers. It is believed that when such catalysts are attached to a solid support, such as silica, polyolefin polymerizations using such supported catalysts provide a polymer composition which possesses a broad compositional distribution. This is believed to be due at least in part to both the creation of unique reaction sites, and the sensitivity of these catalysts to ethylene concentration. These unique reaction sites are believed to result from the unique microenvironments created by the location of the catalyst on the support. The resulting polymer composition, which can be prepared solely from ethylene as an olefin feedstock, is one which is actually a blend or plurality of polymers having a variety of alkyl branched distributions with some catalyst sites giving less branched high density polymer and other sites giving more branched lower density polymer.

When the polymerizations are conducted in the liquid phase, said liquid phase may include solvent or neat monomer. The molar ratio of neutral Lewis acid to transition metal complex can be from 1 to 10000. preferably 10 to 1000. The pressure at which the ethylene polymerizations and copolymerizations take place can be from 1 atmosphere to 1000 atmospheres, preferably 1 to 100 atmospheres.

The polymerizations may be conducted as solution polymerizations as non-solvent slurry type polymerizations, as slurry polymerizations using one or more of the olefins or other solvent as the polymerization medium or in the gas phase. Substantially inert solvents, such as toluene, hydrocarbons, methylene chloride and the like, may be used. Propylene and 1-butene are excellent monomers for use in slurry-type copolymerizations and unused monomer can be flashed off and reused.

Temperature and olefin concentration have significant effects on polymer structure, composition, and molecular weight. Suitable polymerization temperatures are preferably from about −100° C. to about 200° C., more preferably in the 20° C. to 150° C. range.

After the reaction has proceeded for a time sufficient to produce the desired polymers, the polymer can be recovered from the reaction mixture by routine methods of isolation and/or purification.

In general, the polymers of the present invention are useful as components of thermoset materials, as elastomers, as packaging materials, films, compatibilizing agents for polyesters and polyolefins, as a component of tackifying compositions, and as a component of adhesive materials.

High molecular weight resins are readily processed using conventional extrusion, injection molding, compression molding, and vacuum forming techniques well known in the art. Useful articles made from them include films, fibers, bottles and other containers, sheeting, molded objects and the like.

Low molecular weight resins are useful, for example, as synthetic waxes and they may be used in various wax coatings or in emulsion form. They are also particularly useful in blends with ethylene/vinyl acetate or ethylene/methyl acrylate-type copolymers in paper coating or in adhesive applications.

Although not required, typical additives used in olefin or vinyl polymers may be used in the new homopolymers and copolymers of this invention. Typical additives include pigments, colorants, titanium dioxide, carbon black, antioxidants, stabilizers, slip agents, flame retarding agents, and the like. These additives and their use in polymer systems are known per se in the art.

EXAMPLES

Ligand Synthesis

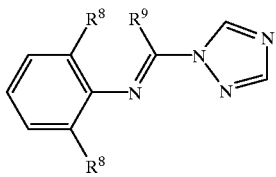

C1: $R^8$=Me, $R^9$=1-naphthyl
C2: $R^8$=iPr, $R^9$=1-naphthyl
C3: $R^8$=Me, $R^9$=phenyl
C4: $R^8$=iPr, $R^9$=phenyl
C5: $R^8$=iPr, $R^9$=2,6-dimethoxyphenyl
C20: $R^8$=Me, $R^9$=2-biphenyl

Example 1

Synthesis of C1. Equimolar amounts of 1,2,4-triazole and N-(2,6-dimethylphenyl)-1-naphthimidoyl chloride (derived in the conventional fashion [H. Ulrich, *The Chemistry of Imidoyl Halides*, Plenum, New York, 1968] from the corresponding amide and phosphorus pentachloride) were treated with an excess of triethylamine in methylene chloride at room temperature. After 1 hour, the solution was concentrated, taken up in ethyl acetate, filtered, and washed sequentially with saturated sodium bicarbonate solution, 0.5 M HCl solution, and brine, then dried over magnesium sulfate, filtered, and concentrated to a syrup Purification by flash chromatography (hexane/EtOAc=4:1) afforded the triazole/imine ligand C1 as a pale yellow solid.

Example 2

Synthesis of C20. A solution of N-(2,6-dimethyl-phenyl)-biphenyl-2-carboximidoyl chloride (833 mg, 2.6 mmol), 1,2,4-triazole (400 mg, 5.8 mmol) and triethylamine (0.5 mL, 3.6 mmol) in $CH_2Cl_2$ (5 mL) was allowed to stand at room temperature for 3 days. The resulting solution was washed with water (50 mL), dried over $Na_2SO_4$ and concentrated in vacuo. The residue was purified by flash chromatography ($SiO_2$, 20% ethyl acetate (EtOAc)/Hexanes) to afford C1 (470 mg, 59%) as a light yellow oil: $R_f$ 0.44 (20% EtOAC/Hexanes); field desorption mass spectrometry (FDMS): m/z 352.

Example 3

Synthesis of C2. A mixture of 1,2,4-triazole (1.2 mmol) and N-(2,6-diisopropylphenyl)-1-naphthimidoyl chloride (0.5 mmol) was treated with triethylamine (1 mmol) and methylene chloride (5 mL) and stirred four hours at room temperature. The reaction was worked up as described in example 1 to afford C2 as a pale yellow solid.

Example 4

Synthesis of C3. A mixture of 1,2,4-triazole (2.9 mmol) and N-(2,6-dimethylphenyl)-1-benzimidoyl chloride (1,5 mmol) was treated with triethylamine (1.5 mmol) and methylene chloride (7 mL) and stirred 14 hours at room temperature. The reaction was worked up as described in example 1 to afford C3 as a pale yellow solid (242 mg)

Example 5

Synthesis of C3. A solution of N-(2,6-dimethylphenyl)-1-benzimidoyl chloride (362 mg, 1.48 mmol) in $CH_2Cl_2$ (7 ml) was treated with 1,2,4-triazole (212 mg, 3.07 mmol) and triethylamine (0.209 ml, 1.49 mmol). The resulting solution was stirred at room temperature overnight. The solvent was removed in vacuo, and the resulting residue was suspended in EtOAc (15 ml) and filtered. The filtrate was washed with 0.5 M HCl (10 ml) and brine (10 ml), dried over $Na_2SO_4$, filtered and concentrated in vacuo. The residue was purified by flash chromatography ($SiO_2$, 70% (EtOAc: Hexanes) to afford C3 (248 mg, 61%): $R_f$ 0.80 (70% EtOAc: Hexanes), $^1$H NMR (300 MHz, $CDCl_3$, TMS reference) δ9.14 (1H, s), 8.08 (1H, s), 7.21–7.38 (5H, m), 6.87–6.98 (3H, M), 2.06 (6H, s), FDMS m/z 276 ($M^+$).

Example 6

Synthesis of C4. A mixture of 1,2,4-triazole (1.5 mmol) and N-(2,6-diisopropylphenyl)-1-benzimidoyl chloride (0 7 mmol) was treated with triethylamine (1 mmol) and methylene chloride (6 mL) and stirred overnight at room temperature. The reaction was worked up as described in example 1 to afford C4 as a pale yellow solid (85 mg) after purification by flash chromatography (hexane/EtOAc=3:1).

Example 7

Synthesis of C4. 1,2,4-Triazole (480 mg, 6.9 mmol) was added to a solution of N-(2,6-diisopropylphenyl)-1-benzimidoyl chloride (1.0 g, 3.3 mmol) in $CH_2Cl_2$ (10 mL). The resulting suspension was treated with triethylamine (2 mL, 14.3 mmol) and allowed to stand at room temperature overnight. The solvent was removed in vacuo and the residue partitioned between EtOAc and $H_2O$. The organic layer was concentrated in vacuo and the residue was purified by flash chromatography ($SiO_2$) to afford C4

Example 8

Synthesis of C5. 2,6-Diisopropylaniline (25 mmol) was added to a chilled suspension of 2,6-dimethoxybenzoyl chloride (25 mmol) in pyridine (20 mL) After stirring three hours, water (50 mL) was added, resulting in a purple precipitate that was isolated by filtration and subsequently recrystallized from ethanol to provide the amide as a purple solid.

A solution of the amide (690 mg, 2 mmol) in acetonitrile (8 mL) was added to a mixture formed by the addition of triethylamine (580 μL) to a cooled suspension of 1,2,4-triazole (420 mg, 6 mmol) and $POCl_3$ in acetonitrile (8 mL). After stirring 24 hours at room temperature, the reaction contents were filtered, and the filtrate was evaporated to an oil. The oil was dissolved in EtOAc, and washed successively with aqueous solutions of sodium bicarbonate, HCl, and NaCl. The organic layer was dried over magnesium sulfate, filtered, and concentrated to an oil. Purification by flash chromatography (hexane/EtOAc=3:1) afforded the desired imino-substituted heterocyclic C5.

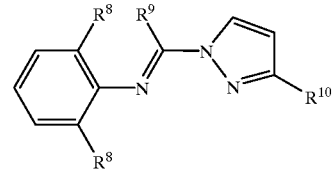

C6: $R^8$=Me, $R^9$=1-naphthyl, $R^{10}$=$CH_3$
C7: $R^8$=iPr, $R^9$=1-naphthyl, $R^{10}$=$CH_3$
C8: $R^8$=Me, $R^9$=1-naphthyl $R^{10}$=H
C8a: $R^8$=iPr, $R^9$=phenyl, $R^{10}$=H

Example 9

Synthesis of C6. A mixture of 3-methylpyrazole (0.8 mmol) and N-(2,6-dimethylphenyl)-1-naphthimidoyl chloride (0.8 mmol) was treated with triethylamine (1.5 mmol) and methylene chloride (5 mL) and stirred 4 hours at room temperature. The reaction was worked up as described in example 1 to afford the desired pyrazole/imine C6.

Example 10

Synthesis of C7. A mixture of 3-methylpyrazole (1.0 mmol) and N-(2,6-diisopropylphenyl)-1-naphthimidoyl chloride (0.7 mmol) was treated with triethylamine (1.0 mmol) and methylene chloride (5 mL) and stirred 1 hour at room temperature. The reaction was worked up as described in example 1 to afford the desired pyrazole/imine C7.

Example 11

Synthesis of C8. A mixture of pyrazole (4.0 mmol) and N-(2,6-dimethylphenyl)-1-naphthimidoyl chloride (1.5 mmol) was treated with triethylamine (2.0 mmol) and methylene chloride (8 mL) and stirred 16 hours at room temperature. The reaction was worked up as described in example 1 to afford the desired pyrazole/imine C8 as pale yellow crystals.

Example 12

Synthesis of C8a. Pyrazole (460 mg, 7.0 mmol) was added to a solution of N-(2,6-diisopropylphenyl)-1-benzimidoyl chloride (1.0 g, 3.3 mmol) in $CH_2Cl_2$ (8 mL). The resulting solution was treated with triethylamine (2 mL. 14.3 mmol) and allowed to stand at room temperature overnight The solution was partitioned between $H_2O$ and EtOAc. The organic layer was washed with HCl (0.2 N), $H_2O$, and brine, dried over $MgSO_4$, filtered and concentrated in vacuo. The residue was dissolved in $CH_2Cl_2$/hexane and treated with methanol (MeOH) to induce crystallization. The crystals were isolated by vacuum filtartion to afford C8a (300 mg, 27%) as off white crystals.

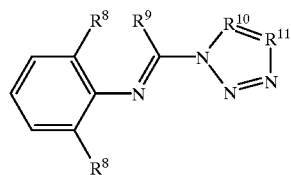

C9: $R^8$=iPr; $R^9$=1-naphthyl; $R^{10}$, $R^{11}$=CH

C10: $R^8$=iPr; $R^9$=phenyl; $R^{10}$, $R^{11}$=C-Ph and N (one C-Ph, one N)

Example 13

Synthesis of C9. A mixture of 1H-1,2,3-triazole (100 μL) and N-(2,6-diisopropylphenyl)-1-naphthimidoyl chloride (200 mg) was treated with triethylamine (150 μl) and methylene chloride (6 mL) and stirred 1 hour at room temperature. The reaction was worked up as described in example 1 to afford the desired triazole/imine C9.

Example 14

Synthesis of C10. A mixture of 5-phenyl-1H-tetrazole (160 mg, 11 mmol) and N-(2,6-diisopropylphenyl)-1-benzimidoyl chloride (07 mmol) was treated with triethylamine (250 μl) and methylene chloride (6 mL) and stirred 16 hours at room temperature. The reaction was worked up as described in example 1. Attempts to further purify the desired product using silica gel chromatography led to ligand decomposition, and thus the crude product of the workup was used directly in the next step to form the nickel complex D10.

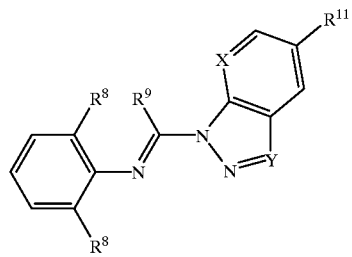

C11: $R^8$=iPr; $R^9$=phenyl; $R^{11}$=COOH; X=CH; Y=N
C12: $R^8$=iPr; $R^9$=phenyl; $R^{11}$=H; X=N; Y=N
C13: $R^8$=iPr; $R^9$=$CF_3$; $R^{11}$=H; X=CH; Y=CH
C14: $R^8$=iPr; $R^9$=$CF_3$; $R^{11}$=$NO_2$; X=CH; Y=CH

Example 15

Synthesis of C11. A mixture of benzotriazole-5-carboxylic acid (163 mg, 1.0 mmol) and N-(2,6-diisopropylphenyl)-1-benzimidoyl chloride (0 7 mmol) was treated with triethylamine (260 μl) and methylene chloride (6 mL) and stirred overnight at room temperature. The reaction was worked up as described in example 1 and purified by flash chromatography (hexane/ethyl acetate=3:1) to afford the desired benzotriazole/imine C11, as well as a contaminant byproduct (MS=689) which may be the diacylated product resulting from acylation of both the desired ring nitrogen and the carboxylic acid.

Example 16

Synthesis of C12 A mixture of 1H-1,2,3-triazolo(4,5-β) pyridine (1.0 mmol) and N-(2,6-diisopropylphenyl)-1-benzimidoyl chloride (0.5 mmol) was treated with triethylamine (1.0 mmol) and methylene chloride (7 mL) and stirred 16 hours at room temperature. The reaction was worked up as described in example 1 and used directly without further purification

Example 17

Synthesis of C13 A solution of indazole (202 mg, 1.71 mmol) in tetrahydrofuran (THF) (5.0 mL) was cooled to 0° C. in an ice bath and treated with NaH (60% dispersion in mineral oil, 106 mg, 2.66 mmol). The resulting suspension was stirred at 0° C. for 25 min, then treated with N-(2,6-diisopropylphenyl)-trifluoroacetimidoyl chloride (497 mg, 1.70 mmol) [which had been prepared according to the procedure of K. Tamura, et al. *J. Org. Chem.* 1993, 58, 32–35, from trifluoroacetic acid, 2,6-diisopropyl aniline, carbon tetrachloride, triphenylphosphine and triethylamine] via syringe, rinsing the syringe with THF (0.5 mL). The ice bath was removed and the suspension allowed to stir at rt for 1.5 h. The solvent was removed in vacuo, and the residue was partitioned between saturated $NaHCO_3$ (5 mL) and $CH_2Cl_2$ (5 mL). The aqueous layer was further extracted with $CH_2Cl_2$ (2×5 mL). The combined organic extracts were dried over $Na_2SO_4$, filtered and concentrated in vacuo. The resulting residue was flash chromatographed (SiO$_2$, 4% EtOAc: Hex) to afford C13 (548 mg, 86%) R$_f$ 0 27 (4% EtOAc: Hex); $^1$H-NMR (300 MHz CDCl$_3$) δ845 (d, 1 H J=8.2 Hz), 8.29 (d, 1 H, J=0.6 Hz), 7.84 (dt, 1 H, J=8.0 Hz, J=1.1 Hz) 7.54 (ddd, 1H, J=8.4 Hz, J=7.1 Hz, J=1.1 Hz), 7.40 (ddd, 1 H, J=8.0 Hz, J=7.1 Hz, J=0.8 Hz), 7.06–7.20 (m, 3H), 2.85 (p, 2H, J=6.9 Hz). 1.20 (d, 6H, J=6.9 Hz), 1.15 (d, 6 H, J=6.6 Hz); IR (film) 2965, 1684, 1431, 1171, 1154, 926 cm$^{-1}$; FDMS m/z 373 (M+, 100%).

C13 was contaminated with a small amount of unidentified impurities: $^1$H NMR (300 MHz, CDCl$_3$) δ7.72 (d, J=9.1 Hz), 2.72 (d, J=6.9 Hz).

Example 18

Synthesis of C14 A solution of 5-nitroindazole (286 mg, 1.75 mmol) in THF (5 mL) was cooled to 0° C. in an ice bath and treated with NaH (60% dispersion in mineral oil, 110 mg, 2.74 mmol). The resulting suspension was stirred at 0° C. for 20 min, then treated with N-(2,6-diisopropylphenyl)-trifluoroacetimidoyl chloride (509 mg, 1.74 mmol) via syringe, rinsing the syringe with THF (0.5 mL). The ice bath was removed, and the suspension stirred at rt for 2 h. The solvent was removed in vacuo, and the residue partitioned between saturated NaHCO$_3$ (5 mL) and CH$_2$Cl$_2$ (5 mL). The aqueous layer was further extracted with CH$_2$Cl$_2$ (2×5 mL). The combined organic extracts were dried over Na$_2$SO$_4$, filtered and concentrated in vacuo. The residue was flash chromatographed (3% EtOAc: Hex) to afford C14 (573 mg, 78%): R$_f$ 0.16 (3% EtOAc: Hex); $^1$H NMR (300 MHz, CDCl$_3$) δ8.80 (dd, 1 H, J=2.2 Hz, J=0.5 Hz), 8.47 (s, 1H), 8.42 (dd, 1H, J=9.2 Hz, J=1.9 Hz), 8.12 (dd, 0.5 H, J=9.8 Hz, J=1.9 Hz), 7.85 (d, 0.5 H. J=9.6 Hz), 7.18–7.22 (m, 3 H), 2.79 (p, 2 H, J=6.9 Hz), 1.20 (br d, 6 H. J=5.8 Hz), 1.16 (br d, 6 H, J=6.0 Hz); IR (Film) 2965, 1686, 1528, 1431, 1345, 1172, 1150, 922; FDMS m/z 418 (M+, 100%).

C14 was contaminated with a small amount of unidentified impurities: $^1$H NMR (300 MHz, CDCl$_3$) δ8.52–8.64 (br m), 2.69 (p, J=69 Hz), 0.85–1.10 (br s).

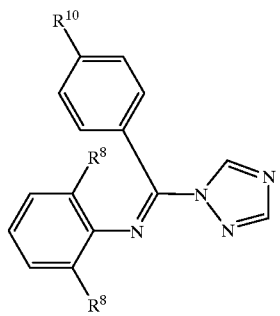

C15: R$^8$=CH$_3$, R$^{10}$=CF$_3$
C16: R$^8$=CH$_3$, R$^{10}$=OCH$_3$
C17: R$^8$=CH$_3$, R$^{10}$=NO$_2$
C18: R$^8$=CH$_3$, R$^{10}$=t-C$_4$H$_9$

Example 19

Synthesis of C15. A solution of N-(2,6-dimethylphenyl)-4-trifluoromethyl-1-benzimidoyl chloride (566.5 mg, 1.8 mmol) in CH$_2$Cl$_2$ (8.6 ml) was treated with 1,2,4-triazole (264 mg, 3.8 mmol) and triethylamine (0.254 ml, 1.8 mmol). The resulting solution was stirred at room temperature overnight, The solvent was removed in vacuo, and the resulting residue was suspended in EtOAc (20 ml) and filtered. The residue was washed with EtOAc (2×5 mL). The combined filtrate was washed with sat'd NaHCO$_3$ (15 mL). 0.5 M HCl (15 mL), and brine (15 ml), dried over Na$_2$SO$_4$, filtered and concentrated in vacuo The residue was purified by flash chromatography (SiO$_2$, 30% EtOAc: Hexanes) to afford C15 (295 mg, 48%): R$_f$ 0.51 (30% EtOAc: Hexanes); $^1$H NMR (300 MHz, CDCl$_3$) δ9.24 (s, 1H), 8.09 (s, 1H), 7.58 (d, 2H, J=8.5 Hz), 7.36 (d, 2 H, J=8.2 Hz), 6.94–7.27 (m, 3H), 2.06 (s, 6H); FDMS m/z 344 (M+, 100%).

Example 20

Synthesis of C16. A solution of N-(2,6-dimethylphenyl)-4-methoxy-1-benzimidoyl chloride (509.5 mg, 1.9 mmol) in CH$_2$Cl$_2$ (8.8 ml) was treated with 1,2,4-triazole (270 mg, 3.9 mmol) and triethylamine (0.260 ml, 1.9 mmol). The resulting solution was stirred at room temperature overnight The solvent was removed in vacuo, and the resulting residue was suspended in EtOAc (20 ml) and filtered. The residue was washed with EtOAc (2×5 mL). The combined filtrate was washed with sat'd NaHCO$_3$ (15 mL), 0.5 M HCl (15mL), and brine (15 ml), died over Na$_2$SO$_4$, filtered and concentrated in vacuo. The residue was purified by flash chromatography (SiO$_2$, 50% EtOAc: Hexanes) to afford C16 (424 mg. 77%): R$_f$ 0.58 (50% EtOAc: Hexanes); $^1$H NMR (300 MHz, CDCl$_3$) δ9.11 (s, 1H), 8.08 (s, 1H), 7.16 (d, 2H, J=8.8 Hz), 6.79 (d, 2H, J=8.5 Hz), 3.78 (s, 3H), 2.05 (s, 6H); FDMS m/z 307 (M+1, 100%).

Example 21

Synthesis of C17. A solution of N-(2,6-dimethylphenyl)-4-nitro-1-benzimidoyl chloride (546.3 mg, 1.9 mmol) in CH$_2$Cl$_2$ (9 ml) was treated with 1,2,4-triazole (271 mg, 3.9 mmol) and triethylamine (0.260 ml, 1.9 mmol). The resulting solution was stirred at room temperature overnight The solvent was removed in vacuo, and the resulting residue was suspended in EtOAc (20 ml) and filtered. The residue was washed with EtOAc (2×10 mL). The combined filtrate was washed with sat'd NaHCO$_3$ (20 mL), 0.5 M HCl (20 mL), and brine (20 ml), dried over Na$_2$SO$_4$, filtered and concentrated in vacuo. The residue was purified by flash chromatography (SiO$_2$, 30% EtOAc: Hexanes) to afford C17: R$_f$ 0.36 (30% EtOAc: Hexanes); $^1$H NMR (300 MHz, CDCl$_3$) δ9.26 (s, 1H), 8.16 (d, 2H, J=8.8 Hz), 8.08 (s, 1H), 7.42 (d, 2H, J=8.8 Hz), 6.94–6.97 (m, 3H), 2.07 (s, 6H); FDMS m/z 321 (M+, 100%).

Example 22

Synthesis of C18. A solution of N-(2,6-dimethylphenyl)-4-(t-butyl)-1-benzimidoyl chloride (506 mg, 1.7 mmol) in CH$_2$Cl$_2$ (5 ml) was treated with 1,2,4-triazole (257 mg, 3.7 mmol) and triethylamine (0.260 ml, 1.9 mmol). The resulting solution was allowed to stand at room temperature for 10 days. The solvent was removed in vacuo. The residue was re-dissolved in a minimal amount of CH$_2$Cl$_2$ and treated with hexane (20 mL). The supernatent was collected by vacuum filtartion and concentrated in vacuo. The residue was purified by flash chromatography (SiO$_2$, 15% EtOAc/hex) to afford C18 (238 mg, 42%) as a yellow solid: R$_f$ 0.35 (15% EtOAc/hex): FDMS: m/z 332.

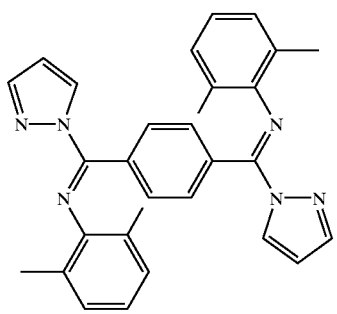

C19

Example 23

Synthesis of C19. CH$_2$Cl$_2$ (5 mL) was added to a mixture of N$^1$,N$^4$-bis(2,6-dimethyl-phenyl)-terephthalodiimidoyl dichloride (1.07 g, 2.45 mmol) and pyrazole (615 mg, 9.03 mmol). The resulting suspension was treated with triethylamine (1 mL, 7.17 mmol), CH$_2$Cl$_2$ (5 mL), triethylamine (1 mL, 7.17 mmol) and CH$_2$Cl$_2$ (5 mL). The resulting solution was stirred at room temperature overnight. The solvent was removed in vacuo and the residue suspended in CH$_2$Cl$_2$/EtOAc/Et$_2$O. The organic mixture was washed several times with H$_2$O and brine, dried over Mg$_2$SO$_4$ filtered and concentrated in vacuo. The residue was purified by flash chromatography (SiO$_2$, 19% EtOAc/hex). After chromatography, the bis(imine/pyrazole) C19 crystallized from the eluent and was collected by vacuum filtration and dried in vacuo to afford C19 (611 mg, 53%), FDMS: m/z 472.

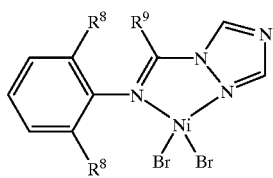

D1: R$^8$=Me, R$^9$=1-naphthyl
D2: R$^8$=iPr, R$^9$=1-naphthyl
D3: R$^8$=Me, R$^9$=phenyl
D4: R$^8$=iPr, R$^9$=phenyl
D5: R$^8$=iPr, R$^9$=2,6-dimethoxyphenyl
D20: R$^8$=Me, R$^9$=2-biphenyl

Example 24

Synthesis of D1. A methylene chloride solution of the triazole/imine C1 (46 mg, 0.14 mmol) and (DME)NiBr$_2$ (37 mg, 0.12 mmol) were combined via stainless steel cannula. The mixture was left to stir at 23° C. for 16 hours. The solvent was partially evaporated under reduced pressure and 10 mL of hexane was added to fully precipitate the complex. The resulting yellow solid was washed with hexane and then placed under high vacuum to remove all solvent. 37 mg of pre-catalyst D1 isolated (60% yield).

Example 25

Synthesis of D20. Methylene Chloride (5 mL) was added to a mixture of triazole/imine C20 (168.2 mg 0.48 mmol) and (diemethyoxyethane(DME))NiBr$_2$ (124.6 mg, 0.40 mmol). The resulting suspension was stirred at room temperature under Ar for 5 min, then an additional portion of ligand (23.3 mg, 0.066 mmol) was added. The resultant suspension was stirred at room temperature for one hour. 2 mL of hexane was added and the resulting supernatent removed via filter tip cannula. The precipitate was dried in vacuo to provide D20 (41 mg) as a green powder.

Example 26

Synthesis of D2. A flame dried Schlenk flask was equipped with a magnetic stir bar and capped with a rubber septum. To the flask was added (DME)NiBr$_2$ (59 mg, 0.191 mmol) and 10 mL of methylene chloride. In a separate flask the imine/triazole C2 (78 mg, 0.204 mmol) was dissolved in 5 mL of methylene chloride and transferred via stainless steel canula onto the (DME)NiBr$_2$ suspension. The mixture was stirred at room temperature for 16 hours. After 16 hours, the methylene chloride was removed in vacuo resulting in a yellow/green solid. The solid was washed with 2×10 mL of hexane. The solid was left to dry under reduced pressure for several hours resulting in 42 mg of the imine/triazole complex D2.

Example 27

Synthesis of D3. Methylene chloride (8 mL) was added to a mixture of triazole/imine C3 (54 mg) and (DME)NiBr$_2$ (57 mg). The reaction was stirred at room temperature overnight. Solvent was removed via filter cannula, and the pale yellow powder was washed with hexane, then dried in vacuo.

Example 28

Synthesis of D3. Methylene Chloride (15 mL) was added to a mixture of triazole/imine C3 (107.4 mg, 0.39 mmol) and (DME)NiBr$_2$ (100 mg, 0.33 mmol). The resultant suspension was stirred at room temperature overnight to afford a green suspension. The solvent was removed under a stream of Ar then in vacuo to afford D3 as a green solid.

Example 29

Synthesis of D4. Methylene chloride (6 mL) was added to a mixture of triazole/imine C4 (60 mg) and (DME)NiBr$_2$ (45 mg). The reaction was stirred at room temperature overnight. The solvent was partially evaporated under a stream of argon, and hexane was added. The precipitated pale green complex was washed several times with hexane, then dried in vacuo.

Example 30

Synthesis of D4. CH$_2$Cl$_2$ (10 mL) was added to a mixture of C4 (114.9 mg, 0.34 mmol) and (DME)NiBr$_2$ (96 mg, 0.31 mmol) in a flame dried Schlenk flask under N$_2$. The resulting suspension was stirred at room temperature under N$_2$ for 42 h, then concentrated under a stream of N$_2$ and in vacuo to afford D4 (160 mg, 97%) as a green powder.

Example 31

Synthesis of D5. Methylene chloride (9 mL) was added to a mixture of ligand C5 (125 mg) and (DME)NiBr$_2$ (83 mg). The reaction was stirred at room temperature overnight. The solvent was partially evaporated under a stream of argon, and hexane was added. The precipitated pale green complex was washed several times with hexane, then dried in vacuo.

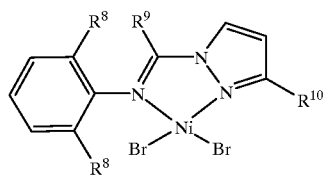

D6: $R^8$=Me, $R^9$=1-naphthyl, $R^{10}$=CH$_3$
D7: $R^8$=iPr, $R^9$=1-naphthyl, $R^{10}$=CH$_3$  D7a: $R^8$=iPr, $R^9$=phenyl, $R^{10}$=H

Example 32

Synthesis of D6. Methylene chloride (10 mL) was added to a mixture of the pyrazole/imine ligand C6 (81 mg, 0.24 mmol) and (DME)NiBr$_2$ (60 mg, 0.19 mmol). The suspension immediately turned a deep orange/brown color, and was allowed to stir 18 hours. The solvent was evaporated under a stream of argon, and the precipitated orange solid was washed several times with hexane and hexane/methylene chloride before drying in vacuo. The pre-catalyst D6 was isolated as an orange/brown powder.

Example 33

Synthesis of D7. A flame dried Schlenk flask was equipped with a magnetic stir bar and capped with a rubber septum. To the flask was added (DME)NiBr$_2$ (71 mg, 0.23 mmol) and 10 mL of methylene chloride. In a separate flask the imine/heterocycle C7 (98 mg, 0.25 mmol) was dissolved in 5 mL of methylene chloride and transferred via stainless steel canula onto the (DME)NiBr$_2$ suspension. The mixture was stirred at room temperature for 16 hours. After 16 hours, the methylene chloride was removed in vacuo resulting in a red/brown solid. The solid was washed with 2×5 mL of hexane. The solid was left to dry under reduced pressure for several hours resulting in 97 mg of the imine/heterocycle complex D7.

Example 34

Synthesis of D7a. CH$_2$Cl$_2$ (14 mL) was added to a mixture of C8a (110 mg. 0.33 mmol) and (DME)NiBr$_2$ (91 mg, 30 mmol) in a flame dried Schlenk flask. The resulting solution was stirred at room temperature for 1 hour, then treated with hexane (10 mL) and concentrated under a stream of N$_2$ until crystallization began The supernatent was removed via filter paper tipped cannula. The crystals were dried in vacuo to afford D7a (128 mg, 80%) as tan crystals.

Synthesis of

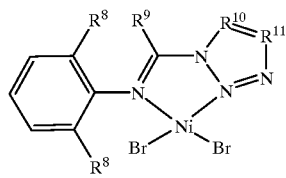

D9: $R^8$iPr; $R^9$=1-naphthyl; $R^{10}$, $R^{11}$=CH
D10: $R^8$=iPr; $R^9$=phenyl; $R^{10}$, $R^{11}$=C-Ph and N (one C-Ph, one N)

Example 35

Synthesis of D9. Methylene chloride (5 mL) was added to a mixture of the triazole/imine ligand C9 (42 mg) and (DME)NiBr$_2$ (200 mg). The suspension was allowed to stir 18 hours, at which time the solvent was evaporated under a stream of argon, and the precipitated yellow-orange solid was washed several times with hexane and hexane/methylene chloride before drying in vacuo.

Example 36

Synthesis of D10. Methylene chloride (7 mL) was added to a mixture of the tetrazole/imine ligand C10 (82 mg) and (DME)NiBr$_2$ (40 mg) The suspension was allowed to stir 18 hours at which time the solvent was evaporated under a stream of argon, and the precipitate pale green solid was washed several times with hexane and hexane/methylene chloride before drying in vacuo.

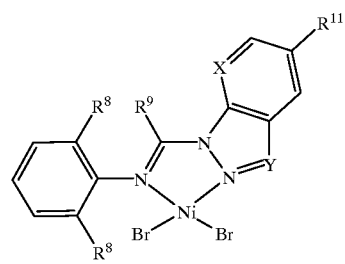

D11: $R^8$=iPr; $R^9$=phenyl; $R^{11}$=COOH, X=CH; Y=N
D12: $R^8$=iPr; $R^9$=phenyl; $R^{11}$=H; X=N; Y=N
D13: $R^8$=iPr; $R^9$=CF$_3$; $R^{11}$=H; X=CH; Y=CH
D14: $R^8$=iPr; $R^9$=CF$_3$; $R^{11}$=NO$_2$; X=CH; Y=CH

Example 37

Synthesis of D11. Methylene chloride (5 mL) was added to a mixture of excess benzotriazole/imine ligand C11 and (DME)NiBr$_2$. The reaction was allowed to stir 18 hours, at which time the solvent was evaporated under a stream of argon, and the precipitated beige solid was washed several times with hexane and hexane/methylene chloride before drying in vacuo.

Example 38

Synthesis of D12 Methylene chloride was added to a mixture of the benzotriazole/imine ligand C12 (82 mg) and a deficiency of (DME)NiBr$_2$ A green precipitate appeared almost immediately The solvent was evaporated under a stream of argon, and the precipitated pale green solid was washed several times with hexane and hexane/methylene chloride before drying in vacuo.

Example 39

Synthesis of D13 A mixture of imine/indazole adduct C13 (112 mg, 0.299 mmol) and (DME)NiBr$_2$ (73 mg, 0.238 mmol) was dissolved in CH$_2$Cl$_2$ (10 mL). The resulting solution was stirred at rt overnight. The suspension was concentrated under a stream of Ar, and the resulting precipitate was washed several times with hexanes. The precipitate was dried In vacuo to afford dibromo complex D13.

Example 40

Synthesis of D14 A mixture of imine/indazole adduct C14 (100 mg. 0.238 mmol) and (DME)NiBr$_2$ (63 mg, 0.206 mmol) was dissolved in CH$_2$Cl$_2$ (10 mL), and stirred at rt overnight. The orange/yellow suspension was concentrated under a stream of Ar, and washed with hexanes (10 mL). The residue was dried in vacuo to afford D14 as an orange solid.

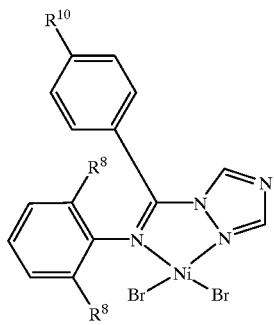

D15: $R^8=CH_3$, $R^{10}=CF_3$
D16: $R^8=CH$, $R^{10}=OCH_3$
D17: $R^8=CH_3$, $R^{10}=NO_2$
D18: $R^8=CH_3$, $R^{10}=t-C_4H_9$

Example 41

Synthesis of D15. Methylene Chloride (15 mL) was added to a mixture of triazole/imine C15 (108.1 mg, 0.31 mmol) and (DME)NiBr$_2$ (72 mg, 0.24 mmol). The resultant suspension was stirred at room temperature for 2 hr to afford a green suspension. The solvent was removed under a stream of Ar then in vacuo to afford D15 as a green solid.

Example 42

Synthesis of D16. Methylene Chloride (15 mL) was added to a mixture of triazole/imine C16 (104.5 mg, 0.34 mmol) and (DME)NiBr$_2$ (84 mg, 0.27 mmol). The resultant suspension was stirred at room temperature for 25 hr to afford a green suspension. The solvent was removed under a stream of Ar then in vacuo to afford D16 as a green solid.

Example 43

Synthesis of D17. A solution of imine/triazole C17 (100 mg, 0.311 mmol) dissolved in CH$_2$Cl$_2$ (15 mL) was added to (DME)NiBr$_2$ (76 mg, 0.249 mmol) in a flame dried Schlenk flask under Ar. The resulting suspension was stirred at rt under Ar overnight. The solvent was removed under a stream of Ar, then in vacuo to afford D17 as a yellow/green solid.

Example 44

Synthesis of D18. Methylene Chloride (10 mL) was added to a mixture of triazole/imine C18 (104 mg, 0.31 mmol) and (DME)NiBr$_2$ (74 mg, 0.25 mmol). The resultant suspension was stirred at room temperature overnight. The solvent was removed under a stream of N$_2$. The residue was washed with hexane (5 mL) then dried in vacuo to afford D18 (89 mg) as a green solid.

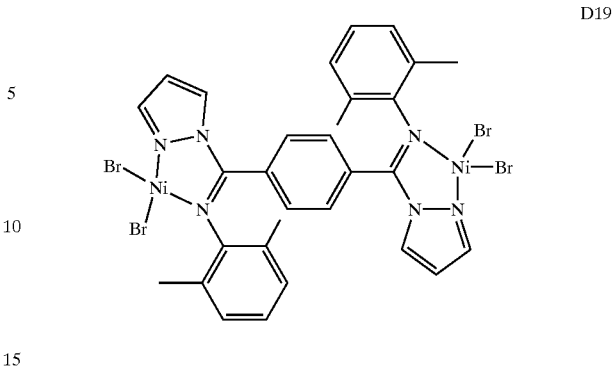

Example 45

Synthesis of D19. CH$_2$Cl$_2$ (10 mL) was added to a mixture of C19 (122 mg. 0.258 mmol) and (DME)NiBr$_2$ (120 mg, 0.392 mmol) in a flame dried Schlenk flask. The resulting suspension was stirred at room temperature overnight, then treated with hexane (10 mL). The solvent was removed via a filter paper tipped canula. The residue was washed with CH$_2$Cl$_2$ (10 mL) and dried in vacuo to afford D19 (167 mg, 94%) as a green solid.

Synthesis of Supported Catalysts

Example 46

Synthesis of the Supported Nickel Complex D19. A flame dried Schlenk flask was charged with the imine/pyrazole complex D19 (45.5 mg, 50.0 μmol) and MAO treated silica (1 g, purchased from Witco TA 02794/HL/04) in an Ar filled dry box. The flask was immersed in an ice water bath under Ar, then CH$_2$Cl$_2$ (25 mL) was added. The resulting suspension was stirred at 0° C. for 20 min then the solvent was removed in vacuo at 0° C. to afford supported D19 as an orange solid.

Example 47

Synthesis of the supported Nickel Complex D18. A flame dried Schlenk flask was charged with the imine/triazole complex D18 (13.3 mg, 24.1 μmol) and MAO treated silica (2.14 g, purchased from Witco TA 02794/HL/04) in an Ar filled dry box. The flask was removed from the box, and immersed in an ice water bath under Ar, then CH$_2$Cl$_2$ (25 mL) was added. The resulting suspension was stirred at 0° C. for 25 min then the solvent was removed in vacuo at 0° C. to afford supported D18.

Polymerizations

Example 48

The triazole/imine complex D1 (2.0 mg) was suspended in 50 mL of dry toluene. The reaction mixture was equilibrated at room temperature under an ethylene atmosphere, then treated with MAO (2.0 mL of a 10% by weight solution in toluene) and stirred under 1 atm ethylene. A white polyethylene precipitate was observed within minutes. After five minutes, the reaction was quenched by the sequential addition of acetone, methanol, and 6M HCl. The precipitate was isolated by filtration, washed, and dried in vacuo to yield 700 mg of polyethylene (85,000 To/h). DSC: $T_m$=123. GPC: $M_w$=23,000.

Example 49

A stock solution of the triazole/imine complex D20 was prepared by suspending complex D20 (4.0 mg, ) in toluene (4.0 mL) and $CH_2Cl_2$ (4.0 mL). 50 mL of toluene was stirred vigorously in an ice bath under 1 atm ethylene in a flame dried Schlenk flask for 20 min. A 10% by weight solution of MAO in toluene (4 mL) was added to the polymerization flask, followed by 2 mL of the nickel complex stock solution. The resulting solution was stirred vigorously under 1 atm ethylene at 0° C. for 40 min The reaction was quenched by sequential addition of MeOH, HCl (6 N) and acetone. The polyethylene was isolated by vacuum filtration and dried in an 80° C. vacuum oven overnight to afford 1.2 g of polyethylene; GPC: $M_n$=2,340, $M_w$=19,800.

Example 50

The triazole/imine complex D3 (2.7 mg) was suspended in 20 mL of dry toluene. The reaction mixture was equilibrated at 0° C. under an ethylene atmosphere, then treated with MAO (2.0 mL of a 10% by weight solution in toluene) and stirred under 1 atm ethylene. After 15 minutes, the reaction was quenched by the sequential addition of acetone, methanol, and 6M HCl. The precipitate was isolated by filtration, washed, and dried in vacuo to yield 747 mg of polyethylene. (19,600 To/h, $M_n$=6900, $M_w$=52,200 (GPC); 2 branches/1000 carbons by $^1H$ NMR).

Example 51

The triazole/imine complex D3 (4.5 mg, 9.05 μmol) was suspended in dry toluene (50 mL) in a flame dried 500 mL round bottom flask fitted with a gas adapter. The suspension was cooled to 0° C. in an ice bath and placed under an ethylene atmosphere (1 atm). A 10% by weight solution of MAO in toluene (2 mL) was added to the polymerization flask. The resulting solution was stirred vigorously under 1 atm ethylene at 0° C. for 20 min, then quenched by sequential addition of acetone, MeOH, and HCl (6 N). The resulting polymer was collected by vacuum filtration and dried in vacuo to afford 2.88 g of polyethylene (34,000 TO/hr, $M_n$=7390, $M_w$=55,200 (GPC); 2 branches/1000 C's ($^1H$ NMR)).

Example 52

The triazole/imine complex D3 (3.8 mg, 7.6 μmol) was suspended in dry toluene (100 mL) in a flame dried 500 mL round bottom flask fitted with a gas adapter. The suspension was immersed in a room temperature water bath and placed under an ethylene atmosphere (1 atm). A 10% by weight solution of MAO in toluene (2 mL) was added to the polymerization flask. The resulting solution was stirred vigorously under 1 atm ethylene at rt for 10 min, then quenched by sequential addition of acetone, MeOH, and HCl (6 N). The resulting polymer was collected by vacuum filtration and dried in vacuo to afford 1.24 g of polyethylene (70,200 TO/hr, $M_n$=2410, $M_w$=18,900 (GPC); 13 branches/ 1000 C's ($^1H$ NMR)).

Example 53

The triazole/imine complex D4 (3.4 mg, 6.4 μmol) was suspended in toluene (50 mL) and cooled to 0–4° C. in an ice water bath under an atmosphere of ethylene. The suspension was stirred vigorously under 1 atm ethylene for 10 min, then treated with a 10% by weight solution of MAO in toluene (4 mL). The resulting suspension was stirred vigorously under an atmosphere of ethylene at 0–4° C. for 10 min, then quenched by sequential addition of MeOH, acetone, and 6N HCl. The precipitated polymer was isolated by vacuum filtration and dried in an 80° C. vacuum oven overnight to afford 1.9 g of polyethylene (66,000 TO/h). $^1H$ NMR: ($M_n$=3014, 13.4 branches/1000 carbons).

Example 54

The pyrazole/imine complex D6 (14.6 mg) was suspended in 18 mL of dry toluene. The reaction mixture was cooled to 0° C. and placed under an ethylene atmosphere. A 10% by weight solution of MAO in toluene (1.8 mL) was added to the polymerization flask. The ice bath was removed and the mixture was left to stir for thirty minutes with substantial evolution of heat. Acetone, 6M HCl, and $H_2O$ were added to quench the polymerization and precipitate the polyethylene. The polymer was isolated by filtration, washed, and dried in vacuo. The procedure was repeated without removing the ice bath, with similar polymer characteristics. In both cases, $^1H$ NMR analysis was consistent with branched polyethylene ($M_n$<5,000).

Example 55

The pyrazole/imine complex D7a (5.2 mg, 9.4 μmol) was dissolved in toluene (50 mL) under an atmosphere of ethylene. The resulting solution was stirred vigorously under 1 atm of ethylene, then treated with a 10% by weight solution of MAO in toluene (4 mL) and stirred vigorously under 1 atm of ethylene at room temperature for 80 min. The reaction was quenched by sequential addition of MeOH, 6N HCl, and acetone. The organic layer was separated, washed with $H_2O$, and concentrated in vacuo. The resulting viscous oil was treated with MeOH and concentrated in vacuo to afford 4.0 g of polyethylene (11,400 TO/h). $^1H$ NMR: ($M_n$=1162; 74.6 branches(1000 carbons).

Example 56

The triazole/imine complex D9 (4.0 mg) was suspended in 18 mL of dry toluene. The reaction mixture was cooled to 0° C. and placed under an ethylene atmosphere. A 10% by weight solution of MAO in toluene (1.8 mL) was added to the polymerization flask. The mixture was left to stir for 45 minutes at 0° C. Acetone, 6M HCl, and $H_2O$ were added to quench the polymerization. No precipitated polyethylene was observed. Separation and subsequent evaporation of the aqueous layer yielded a small amount of solid. The reaction was repeated at room temperature, and a small amount of amorphous material was recovered.

Example 57

A 250 mL flame dried Schlenk flask was charged with bis(1,5-cyclooctadiene) nickel(0) (14.0 mg, 0.051 mmol), $HBAr_4$ (Ar=3,5-bis (trifluoromethyl)phenyl) (39.4 mg, 0.046 mmol) and imine/indazole adduct C13 (13.7 mg, 0.037 mmol). The flask was evacuated and backfilled with ethylene, then charged with toluene (30 mL) resulting in the formation of a dark green/blue solution. The reaction exothermed to ~45° C., and was allowed to stir under ethylene (1 atm) with no temperature control for 1.5 h, after which it was quenched by the addition of acetone and MeOH. The solvent was removed in vacuo to afford an oily waxy solid (2.83 g): GPC: $M_n$=327; $M_w/M_n$=9; $^1H$ NMR: 92 branches/ 1000 carbon atoms.

Example 58

A 250 mL flame dried Schlenk flask was charged with bis(1,5-cyclooctadiene) nickel(0) (8.5 mg, 0.031 mmol), $HBAr_4$ (Ar=3,5-bis (trifluoromethyl)phenyl) (24.3 mg, 0.028 mmol) and imine/indazole adduct C14 (11.0 mg, 0.026 mmol). The flask was evacuated and backfilled with ethylene, then charged with toluene (30 mL) resulting in the formation of an orange/brown solution. The reaction was allowed to stir under ethylene (1 atm) at rt for ~1.33 h, after which it was quenched by the addition of acetone and MeOH. The resulting polyethylene was collected by vacuum filtration, and dried in vacuo to afford a white polyethylene (117.2 mg): GPC: $M_n$=5710; $M_w/M_n$=4.7; $^1$H NMR: 42 branches/1000 carbon atoms.

Example 59

A flame dried Schlenk flask was charged with complex D7 (6 mg, 0.0098 mmol) and 50 mL of toluene. The flask was then cooled to 0° C. in an ice bath. MAO (1.5 mL of a 10 wt. % solution in toluene) was then added to the suspension and the reaction left to stir for 30 minutes. Acetone, methanol and 6M HCl were added to quench the reaction and precipitate the resulting branched polyethylene ($^1$H NMR $M_n$=2500).

Example 60

A flame dried Schlenk flask was charged with complex D1 (5 mg. 0.0092 mmol), norbornene (2 g) and 50 mL of toluene. The flask was then placed in a water bath (23° C.) to control reaction temperature. MAO (2 mL of a 10 wt % solution in toluene) was then added to the suspension and the reaction left to stir for 16 hours. Acetone and methanol were added to quench the reaction and precipitate the resulting polynorbornene. The polymer was collected by filtration and washed with 6M HCl, water, and acetone. The polymer was dried in a vacuum oven resulting in 700 mg of polynorbornene. GPC: $M_n$=14,500; $M_w$=44,000.

Example 61

A flame dried Schlenk flask was charged with complex D4 (6 mg, 0.0091 mmol), 1 atmosphere ethylene and 50 mL of toluene. The flask was then placed in a water bath (23° C.) to control reaction temperatue. MAO (2 mL of a 10 wt. % solution in toluene) was then added to the suspension and the reaction left to stir for 20 minutes (polymer began to precipitate within minutes). Acetone, methanol and 6M HCl were added to quench the reaction and precipitate the resulting polyethylene. The polymer was dried in a vacuum oven resulting in 400 mg of polyethylene. GPC: $M_n$=2100; $M_w$=5600. $^1$H NMR: 30 branches/1000 carbon atoms. DSC: $T_m$=104° C.

Example 62

A flame dried Fisher-Porter bottle was charged with complex D2 (5 mg, 0.0083 mmol) and 50 mL of toluene. The flask was placed in a water bath (23° C.) to control reaction temperatue. MAO (2 mL of a 10 wt. % solution in toluene) was then added to the suspension and the bottle rapidly pressurized to 45 psig and the reaction left to stir for 20 minutes. Acetone, methanol and 6M HCl were added to quench the reaction and precipitate the resulting polyethylene. The polymer was dried in a vacuum oven resulting in 150 mg of polyethylene. GPC: $M_w$=22,000. $^1$H NMR: 7 branches/1000 carbon atoms. DSC: $T_m$=127° C.

Example 63

A flame dried Schlenk flask was charged with complex D4 (2 mg, 0.0036 mmol), 1 atmosphere ethylene and 50 mL of toluene. The flask was then placed in an ice-water bath (0° C.) to control reaction temperatue. MAO (2 mL of a 10 wt. % solution in toluene) was then added to the suspension and the reaction left to stir for 10 minutes (polymer began to precipitate within minutes). Acetone, methanol and 6M HCl were added to quench the reaction and precipitate the resulting polyethylene. The polymer was dried in a vacuum oven resulting in 560 mg of polyethylene (33,000 TO/h). GPC: $M_n$=5500; $M_w$=27,000. $^1$H NMR: 4 branches/1000 carbon atoms. DSC: $T_m$=130° C.

Example 64

A flame dried Schlenk flask was charged with complex D4 (2 mg, 0.0036 mmol), 1 atmosphere ethylene and 50 mL of toluene. The flask was then placed in a water bath (23° C.) to control reaction temperature. MAO (2 mL of a 10 wt. % solution in toluene) was then added to the suspension and the reaction left to stir for 10 minutes (polymer began to precipitate within minutes). Acetone, methanol and 6M HCl were added to quench the reaction and precipitate the resulting polyethylene. The polymer was dried in a vacuum oven resulting in 490 mg of polyethylene (30,000 TO/h). GPC: $M_n$=1600; $M_w$=6100. $^1$H NMR: 20 branches/1000 carbon atoms. DSC. $T_m$=110° C.

Example 65

The triazole/imine complex D15 (2.1 mg, 3.7 $\mu$mol) was suspended in dry toluene (100 mL) in a flame dried 500 mL round bottom flask fitted with a gas adapter. The suspension was cooled to 0° C. in an ice bath and placed under an ethylene atmosphere (1 atm). A 10% by weight solution of MAO in toluene (2 mL) was added to the polymerization flask. The resulting solution was stirred vigorously under 1 atm ethylene at 0° C. for 20 min, then quenched by sequential addition of acetone, MeOH, and HCl (6 $\underline{N}$). The resulting polymer was collected by vacuum filtration and dried in vacuo to afford 1.034 g of polyethylene (29,900 TO/hr, $M_n$=8,190, $M_w$=50,300 (GPC); 2 branches/100 C's ($^1$H NMR)).

Example 66

The triazole/imine complex D16 (1.6 mg, 3.03 $\mu$mol) was suspended in dry toluene (100 mL) in a flame dried 500 mL round bottom flask fitted with a gas adapter. The suspension was cooled to 0° C. in an ice bath and placed under an ethylene atmosphere (1 atm). A 10% by weight solution of MAO in toluene (1.5 mL) was added to the polymerization flask. The resulting solution was stirred vigorously under 1 atm ethylene at 0° C. for 20 min, then quenched by sequential addition of acetone, MeOH, and HCl (6 $\underline{N}$). The resulting polymer was collected by vacuum filtration and dried in vacuo to afford 0.338 g of polyethylene (12,000 TO/hr, $M_n$=12,300, $M_w$=53,300 (GPC); 2 branches/100 C's ($^1$H NMR)).

Example 67

The triazole/imine complex D17 (2.6 mg, 4.8 $\mu$mol) was suspended in dry toluene (100 mL) in a flame dried 500 mL round bottom flask fitted with a gas adapter. The suspension was cooled to 0° C. in an ice bath and placed under an ethylene atmosphere (1 atm). A 10% by weight solution of MAO in toluene (2.0 mL) was added to the polymerization flask The resulting suspension was stirred vigorously under 1 atm ethylene at 0° C. for 16 min, then quenched by sequential addition of acetone, MeOH, and HCl (6 $\underline{N}$). The resulting polymer was collected by vacuum filtration and dried in vacuo to afford a small amount of polyethylene.

Example 68

The triazole/imine complex D18 (16.6 mg) was suspended in $CH_2Cl_2$ (16.6 mL). Toluene (50 mL) was charged to a flame dried Schlenk flask under 1 atm ethylene and cooled to 0–4° C. in an ice bath. The toluene was stirred vigorously for 20 min, then treated with a 10% by weight solution of MAO in toluene (4 mL) and stirring continued for 5 min. The complex D18 suspension (2 mL) was added, and the reaction was stirred vigorously under 1 atm of ethylene in an ice water bath for 10.5 min. The reaction was quenched by the sequential addition of MeOH, HCl (6N) and acetone. The polyethylene was isolated by vacuum filtration and dried in a vacuum oven to afford 2.4 g (135,000 TO/h) of polyethylene. $^1$Hnmr: ($M_n$=4087; 7.5 branches/1000 carbons).

Example 69

The triazole/imine complex D18 (4.6 mg, 8.3 μmol) was suspended in $CH_2Cl_2$ (10 mL). Toluene (50 mL) was charged to a flame dried Schlenk flask under 1 atm of ethylene. The toluene was stirred vigorously under 1 atm ethylene for 10 min, then treated with a 10% by weight solution of MAO in toluene (4 mL). The complex suspension (1 mL, 0.46 mg, 0.83 μmol) was added and the resulting solution was stirred vigorously under 1 atm ethylene at room temperature for 45 min, then quenched by sequential addition of MeOH, acetone and 6 N HCl. The precipitated polymer was collected by vacuum filtration and dried in vacuo at 80° C. overnight to afford 1.68 g of polyethylene (95,600 TO/h). $^1$Hnmr: ($M_n$=2032; 8.4 branches/1000 carbons).

Example 70

A 600 mL Parr® autoclave was first heated to ~100° C. under dynamic vacuum to ensure the reactor was dry. The triazole/imine complex D18 (4.6 mg, 8.3 μmol) was suspended in $CH_2Cl_2$ (10 mL). Toluene (150 mL) and a 10% by weight solution of MAO in toluene (4 mL) were added sequentially to the reactor. The reactor was pressurized to 300 psig with ethylene, then vented to ambient pressure. The above prepared complex suspension (1.0 mL, 0.83 μmol) was added and the reactor was quickly pressurized to 300 psig ethylene. After 45 min at 24° C. under 300 psig ethylene, the reactor was vented and the reaction quenched by the addition of acetone. The resulting suspension was slurried with MeOH and 6N HCl, and the polymer was isolated by vacuum filtration, then dried in vacuo at 80° C. overnight to afford 1.42 g of polyethylene (86,462 TO/h). $^1$Hnmr: ($M_n$=3426; 1.9 branches/1000 carbons).

Example 71

The pyrazole/imine complex D19 (2.2 mg, 2.4 μmol) was suspended in toluene (50 mL) under 1 atm of ethylene in a flame dried Schlenk flask immersed in a room temperature water bath. The mixture was allowed to equilibrate under 1 atm ethylene for 10 min, then a 10% by weight solution of MAO in toluene (4mL) was added. The reaction was stirred vigorously under 1 atm ethylene at rt for 29 min, then quenched by sequential addition of MeOH, 6N HCl and acetone. The polymer was collected by vacuum filtration and dried in vacuo overnight at 80° C. to afford 600 mg of polyethylene (9,100 TO/h). $^1$Hnmr: ($M_n$=3107; 28.6 branches/1000 carbons).

Example 72

The imine/pyrazole complex D19 (5.2 mg, 5.7 μmol) was suspended in toluene (50 mL) under 1 atm ethylene in a 200 mL flame dried Schlenk flask immersed in an ice water bath. The mixture was stirred vigorously under 1 atm ethylene at 0° C. for 20 min, then treated with a 10% by weight solution of MAO in toluene (4 mL). The resulting suspension was stirred vigorously under 1 atm ethylene while warming to ~10° C. for 75 min. The reaction was quenched by the sequential addition of MeOH and 6 N HCl. The precipitated polymer was isolated by vacuum filtration and dried in vacuo at 80° C. overnight to afford 1.22 g of polyethylene (1700 TO/h). $^1$H NMR: ($M_n$=12649; 9.8 branches/1000 carbons).

Example 73

A 600 mL Parr® autoclave was first heated to ~100° C. under dynamic vacuum to ensure the reactor was dry. The pyrazole/imine complex D19 (7.5 mg, 8.25 μmol) was charged to the autoclave in an Ar filled glove box. Toluene (150 mL) was charged to the reactor under a stream of Ar. The autoclave was rapidly pressurized to 800 psig ethylene. The pressure was relieved to ambient pressure, and the reaction mixture was treated with a 10% by weight solution of MAO in toluene (4 mL). The reactor was immediately pressurized to 300 psig ethylene, and stirred vigorously at 30° C. for 120 min. The pressure was relieved, and the reaction quenched with MeOH. The contents of the reactor were slurried with MeOH, acetone and 6 N HCl. The polymer was collected by vacuum filtration and dried in vacuo at 80° C. to afford 21.85 g of polyethylene (23,600 TO/h). $^1$H NMR: ($M_n$=4024; 4.1 branches/1000 carbons)

Example 74

A 600 mL Parr® autoclave was first heated to ~100° C. under dynamic vacuum to ensure the reactor was dry. The pyrazole/imine complex D19 (7.2 mg, 7.9 μmol) was charged to the autoclave in an Ar filled glove box. Toluene (150 mL) was charged to the reactor under a stream of Ar. The autoclave was rapidly pressurized to 200 psig ethylene. The, pressure was relieved to ambient pressure, and the reaction mixture was treated with a 10% by weight solution of MAO in toluene (4 mL). The reactor was immediately pressurized to 300 psig ethylene and heated to 45° C. over 2 min. The reaction was stirred vigorously at 45° C. for 90 min. The pressure was relieved, and the reaction quenched with acetone. The contents of the reactor were slurried with MeOH, acetone and 6 N HCl. The polymer was collected by vacuum filtration and dried in vacuo at 80° C. to afford 47.4 g of polyethylene (70,500 TO/h). $^1$H NMR: ($M_n$=5066; 9.2 branches/1000 carbons).

Example 75

A 600 mL Parr® autoclave was first heated to ~120° C. under dynamic vacuum to ensure the reactor was dry. A 1 mg/mL stock solution of imine/pyrazole complex D19 in o-difluorobenzene was prepared. Toluene (150 mL) and a 10% by weight solution of MAO in toluene (4 mL) were added sequentially to the reactor. The reactor was pressurized to 150 psig ethylene, then vented to ambient pressure. The pressurization and venting was repeated while the autoclave was heated to 51° C. The reactor was pressurized to 150 psig ethylene, the above prepared stock solution (2.0 mL, 2.2 μmol) was injected and the reactor heated to 60° C. After 22 min at 60° C. under 150 psig ethylene, the reactor was vented and the reaction quenched by the addition of MeOH (2×2 mL). The resulting suspension was slurried with MeOH, acetone and 6N HCl, and the polymer was isolated by vacuum filtration, then dried in vacuo at 80° C.

overnight to afford 11.9 g of polyethylene (257,000 TO/h). $^1$H NMR: ($M_n$=1926; 19.5 branches/1000 carbons).

Example 76

A 600 mL Parr® autoclave was first heated to ~120° C. under dynamic vacuum to ensure the reactor was dry. A 1 mg/mL stock solution of imine/pyrazole complex D19 in o-difluorobenzene was prepared. Toluene (150 mL) and a 10% by weight solution of MAO in toluene (4 mL) were added sequentially to the reactor. The reactor was pressurized to 300 psig ethylene, then vented to ambient pressure while the autoclave was heated to 53° C. The reactor was pressurized to 150 psig ethylene, the above prepared stock solution (2.0 mL, 2.2 μmol) was injected and the reactor heated to 60° C. and pressurized to 300 psig ethylene. After 11 min at 60° C. under 300 psig ethylene, the reactor was vented and the reaction quenched by the addition of MeOH (2×2 mL). The resulting suspension was slurried with MeOH, acetone and 6N HCl, and the polymer was isolated by vacuum filtration, then dried in vacuo at 80° C. overnight to afford 5.68 g of polyethylene (252,000 TO/h). $^1$H NMR: ($M_n$=2024; 19.9branches/1000 carbons).

Example 77

A 600 mL Parr® autoclave was first heated to ~120° C. under dynamic vacuum to ensure the reactor was dry. A 1 mg/mL stock solution of imine/prazole complex D19 in o-difluorobenzene was prepared. Toluene (150 mL) and a 10% by weight solution of MAO in toluene (4 mL) were added sequentially to the reactor. The reactor was pressurized to 150 psig ethylene, then vented to ambient pressure. The reactor was pressurized to 150 psig ethylene, the above prepared stock solution (2.0 mL, 2.2 μmol) was injected and the reactor heated to 60° C. and pressurized to 300 psig ethylene. After 33 min at 60° C. and 300 psig ethylene, the reactor was vented and the reaction quenched by the addition of MeOH (2×2 mL). The resulting suspension was slurried with MeOH, acetone and 6N HCl. and the polymer was isolated by vacuum filtration, then dried in vacuo at 80° C. overnight to afford 13.3 g of polyethylene (196,000 TO/h). $^1$H NMR: ($M_n$=2122; 17.9 branches/1000 carbons)

Example 78

A 600 mL Parr® autoclave was first heated to ~120° C. under dynamic vacuum to ensure the reactor was dry. A 0.5 mg/mL stock solution of imine/prazole complex D19 in o-difluorobenzene was prepared. Toluene (230 mL) and a 10% by weight solution of MAO in toluene (4 mL) were added sequentially to the reactor. The reactor was pressurized to 300 psig ethylene, then vented to ambient pressure. The reactor was pressurized to 150 psig ethylene and heated to 57° C., and the above prepared stock solution (2.0 mL, 1.1 μmol) was injected and the reactor heated to 60° C. and pressurized to 300 psig ethylene. After 66 min at 60° C. and 300 psig ethylene, the reactor was vented and the reaction quenched by the addition of MeOH (2×2 mL). The resulting suspension was slurried with MeOH acetone and 6N HCl, and the polymer was isolated by vacuum filtration. then dried in vacuo at 80° C. overnight to afford 8.3 g of polyethylene (245,000 TO/h). $^1$H NMR ($M_n$=2652. 16.2 branches/1000 carbons)

Example 79

A 600 mL Parr® autoclave was first heated to ~120° C. under dynamic vacuum to ensure the reactor was dry. A 1.0 mg/mL stock solution of imine/prazole complex D19 in o-difluorobenzene was prepared. Toluene (245 mL) was added, and the reactor was heated to 80° C. A 10% by weight solution of MAO in toluene (4 mL) was added to the reactor under an Ar purge. The reactor was pressurized to 300 psig ethylene, then vented to ambient pressure. The reactor was pressurized to 150 psig ethylene and the above prepared stock solution (2.0 mL, 2.2 μmol) was injected and the reactor pressurized to 300 psig ethylene. After 22 min at 80° C. and 300 psig ethylene, the reactor was vented and the reaction quenched by the addition of MeOH (2×2 mL). The resulting suspension was slurried with 6N HCl, and the polymer was isolated by vacuum filtration to afford 0.20 g of polyethylene. The organic layer from the filtrate was concentrated in vacuo to afford 0.50 g of polyethylene. $^1$H NMR: ($M_n$=3101; 23.7 branches/1000 carbons).

Supported Catalyst Polymerizations

Example 80

Polymerization of Ethylene Using the Supported Catalyst Prepared in Example 46. A 600 mL Parr® autoclave was first heated to about 100° C. under dynamic vacuum to ensure the reactor was dry. The reactor was then purged with argon. The 600 mL Parr® autoclave was charged in the glove box with vacuum oven dried NaCl (200 mg), the supported catalyst prepared in Example 46 (120 mg, 5.55 μmol Ni) and an additional 103 mg NaCl. The autoclave was removed from the dry box, heated to 57° C. with stirring, then pressurized to 300 psig ethylene. After 1 hr at 57–60° C., the pressure was relieved and the reaction quenched in hot $H_2O$ then MeOH. The precipitated polymer was isolated by vacuum filtration and dried in vacuo at 80° C. overnight to afford 0.82 g of polyethylene (5300 TO/h). $^1$H NMR: ($M_n$=4902; 16.3 branches/1000 carbons).

Example 81

A 200 mL flame dried Schlenk flask was charged with the supported catalyst prepared in example 47 (240 mg, 2.6 μmol Ni) in an Ar filled dry box. The flask was removed from the dry box and immersed in an ice water bath under Ar. The flask was evacuated and refilled with 1 atm of ethylene, then toluene (50 mL) was immediately added. The resulting suspension was stirred vigorously under 1 atm of ethylene at 0° C. for 2 h 45 min. The reaction was quenched by the sequential addition of MeOH and 6 N HCl. The precipitated polymer was isolated by vacuum filtration and dried in vacuo at 80° C. to afford 1.046 g of polyethylene (5,200 TO/h). $^1$H NMR: ($M_n$=12898; 3.7 branches/1000 carbons).

Example 82

A 200 mL flame dried Schlenk flask was charged with the supported catalyst prepared in example 47 (199.5 mg, 2.2 μmol Ni) in an Ar filled dry box. The flask was removed from the dry box and immersed in a room temperature water bath under Ar. The flask was evacuated and refilled with 1 atm of ethylene, then toluene (50 mL) was immediately added. The resulting suspension was stirred vigorously under 1 atm of ethylene at rt for 2 h 40 min. The reaction was quenched by the sequential addition of MeOH and 6 N HCl. The precipitated polymer was isolated by vacuum filtration and dried in vacuo at 80° C. to afford 1.018 g of polyethylene (6.200 TO/h). $^1$H NMR: ($M_n$=10615; 5.5 branches/1000 carbons)

Example 83

Polymerization of Ethylene Using the Supported Catalyst Prepared in Example 47. A 600 mL Parr® autoclave was first heated to about 100° C. under dynamic vacuum to ensure the reactor was dry. The reactor was then purged with argon. The 600 mL Parr® autoclave was charged in the glove box with vacuum oven dried NaCl (300 mg) and the supported catalyst prepared in Example 47 (100 mg, 1.09 μmol Ni). The autoclave was removed from the dry box then pressurized to 800 psig ethylene. After stirring 40 min at 23° C. and 800 psig ethylene, the pressure was relieved and the reaction quenched in hot $H_2O$. The precipitated polymer was isolated by vacuum filtration and dried in vacuo at 80° C. overnight to afford 0.328 g of polyethylene (16,120 TO/h). $^1$H NMR: ($M_n$=10189; 5.5 branches/1000 carbons).

Example 84

Polymerization of Ethylene Using the Supported Catalyst Prepared in Example 47. A 600 mL Parr® autoclave was first heated to about 100° C. under dynamic vacuum to ensure the reactor was dry. The reactor was then purged with argon. The 600 mL Parr® autoclave was charged in the glove box with vacuum oven dried NaCl (300 mg) and the supported catalyst prepared in Example 47 (199 mg, 2.2 μmol Ni). The autoclave was removed from the dry box then pressurized to 800 psig ethylene. After stirring 22 min at 24° C. and 800 psig ethylene, the pressure was relieved and the reaction quenched in hot $H_2O$. The precipitated polymer was isolated by vacuum filtration and dried in vacuo at 80° C. overnight to afford 0.552 g of polyethylene (24,440 TO/h). $^1$H NMR: ($M_n$=4838; 6.1 branches/1000 carbons).

Ligand Synthesis

Example 85

This example illustrates the preparation of a compound IV having the formula:

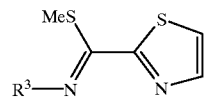

IV for use in a catalyst system according to the present invention

2-Thiazolecarboxylic acid (0.1 mol) is reacted with 1,1'-carbonyldiimidazole (0.1 mol) and 2,6-diisopropylaniline (0.1 mol) to obtain the corresponding amide. This is reacted with Lawesson's reagent to form the thioamide, which is treated with MeI and base to give compound IV.

Synthesis of the Metal Complex

Example 86

This example illustrates the synthesis of a metal complex having the formula V:

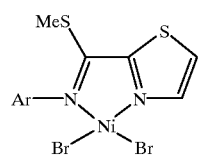

V wherein: Ar=2,6-diisopropylphenyl.

A 50 mL Schlenk flask equipped with a magnetic stir bar and capped with a septum is charged with 0.2 mmol of compound IV from example 85 and 0.2 mmol (1,2-dimethoxyethane)nickel(II) dibromide (Aldrich) under an inert atmosphere. Dry, deoxygenated dichloromethane (5 mL) is added and the mixture is stirred under an argon atmosphere, slowly preparing a crystalline precipitate. After 1 h, another 5 mL dichloromethane is added. The mixture is stirred another 21 h at 21° C., then diluted with 10 mL dry. deoxygenated hexane and stirred another 8 h. The supernatant is removed via a filter paper-tipped cannula, and the residue dried in vacuo at 1 mm Hg to afford complex V.

Olefin Polymerization

Example 87

A 200 mL pear-shaped Schlenk flask equipped with a magnetic stir bar and capped with a septum is charged with 10 mg of compound V. The flask is evacuated and refilled with ethylene, then charged with 75 mL dry, deoxygenated toluene. The resultant suspension is cooled to 0° C. and allowed to equilibrate with 1 atm ethylene for 15 min, then treated with 40 mL of a 10 wt % solution of MAO in toluene (Aldrich) and stirred under 1 atm ethylene. After 60 minutes, the reaction is quenched by the addition of methanol, acetone and 6 N aqueous HCl to produce a polyethylene precipitate.

Ligand Synthesis

Example 88

This example illustrates the preparation of a compound VI having the formula:

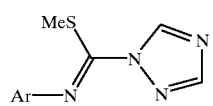

VI wherein: Ar=2,6-diisopropylphenyl, for use in a catalyst system according to the present invention.

Thiophosgene (0.1 mol) is reacted with 1,2,4-triazole (0.2 mol) and base to afford thiocarbonylditriazole. This is heated with 2,6-diisopropylaniline (0.1 mol) to obtain the mixed thiourea, which is treated with MeI (methyl-iodine) and base to give compound VI.

Synthesis of the Metal Complex

Example 89

This example illustrates the synthesis of a metal complex having the formula VII:

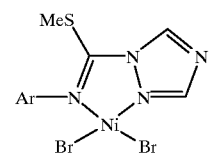

VII wherein: Ar=2,6-diisopropylphenyl.

A 50 mL Schlenk flask equipped with a magnetic stir bar and capped with a septum is charged with 0.2 mmol of compound VI from example 88 and 0.2 mmol (1,2-dimethoxyethane)nickel(II) dibromide (Aldrich) under an inert atmosphere. Dry, deoxygenated dichloromethane (5 mL) is added and the mixture is stirred under an argon atmosphere, slowly preparing a crystalline precipitate. After 1 hour, another 5 mL dichloromethane is added. The mixture is stirred another 21 hour at 21° C., then diluted with 10 mL dry, deoxygenated hexane and stirred another 8 hour. The supernatant is removed via a filter paper-tipped cannula, and the residue dried in vacuo at 1 mm Hg to afford compound VII.

Olefin Polymerization

Example 90

A 200 mL pear-shaped Schlenk flask equipped with a magnetic stir bar and capped with a septum is charged with 10 mg of compound VII from example 89. The flask is evacuated and refilled with ethylene, then charged with 75 mL dry, deoxygenated toluene. The resultant suspension is cooled to 0° C. and allowed to equilibrate with 1 atm ethylene for 15 min, then treated with 4.0 mL of a 10 wt % solution of MAO in toluene (Aldrich) and stirred under 1 atm ethylene. After 60 minutes, the reaction is quenched by the addition of methanol, acetone and 6 N aqueous HCl to produce a polyethylene precipitate.

Ligand Synthesis

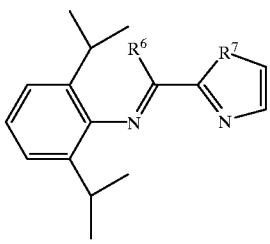

E1: $R^6$=Me, $R^7$=S
E2: $R^6$=H, $R^7$=N(H)

Example 91

Synthesis of E1

A cooled solution of 2-acetylthiazole (4 mmol) and 2,6-diisopropylaniline (12 mmol) in toluene (15 mL) is treated with $TiCl_4$ (2,0 mL of 1.0 M solution in toluene), immediately yielding an olive green precipitate. After allowing the reaction to warm to room temperature, stirring is continued for 72 hours before the reaction contents are filtered through alumina, rinsing with ethyl acetate. The filtrate is washed sequentially with 0.6 M HCl, saturated sodium bicarbonate, and brine, then dried over magnesium sulfate, filtered, and concentrated to afford E1 as a yellow solid Example 92

Synthesis of E2

2-Imidazolecarboxaldehyde (2.9 mmol) is added to a solution of diisopropylaniline (2.9 mmol) in ethanol (10 mL). The reaction is refluxed for 4 hours, then concentrated to a small volume, taken up in ethyl acetate, and washed. Removal of solvent by rotary evaporation gives an oil that crystallized over time, is isolated by filtration, washed, and used without further purification.

Synthesis of the Metal Complex

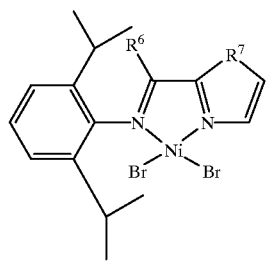

F1: $R^6$=Me, $R^7$=S
F2: $R^6$=H, $R^7$=N(H)

Example 93

Synthesis of F1

A molar excess of thiazole/imine E1, from Example 91, and $(DME)NiBr_2$ are combined as solids in an inert atmosphere glove box. then removed from the glove box and treated with dry $CH_2Cl_2$. The suspension immediately develops a deep orange/brown color and is stirred overnight at room temperature. The solvent is evaporated under a stream of argon, and the precipitated solid is washed several times with hexane and hexane/methylene chloride before being dried in vacuo to give the pre-catalyst F1 as an orange/brown powder.

Example 94

Synthesis of F2

Methylene chloride (10 mL) is added to a mixture of crude imidazole/imine E2 (100 mg) from example 92, and $(DME)NiBr_2$ (27 mg) The suspension gradually develops a bright green color, then appears to darken somewhat. After stirring overnight, the solvent is evaporated under a stream of argon, and the precipitated solid is washed several times with hexane and hexane/methylene chloride before being dried in vacuo to give the pre-catalyst F2 as a yellow-green powder.

Olefin Polymerization

Example 95

The thiazole/imine complex F1 (12 mg), from Example 93, is suspended in 20 mL of dry toluene. The reaction mixture is cooled to 0° C. and equilibrated under an ethylene atmosphere, then treated with MAO (1.8 mL of a 10% by weight solution in toluene) and stirred under 1 atm ethylene for 30 minutes. The reaction is quenched by the sequential addition of acetone, methanol, and 6M HCl. The precipitated polyethylene is isolated by filtration, washed, and dried in vacuo.

Example 96

Polymerization of ethylene with catalyst system IV.

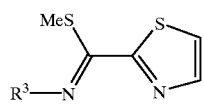

A 500 mL round bottom flask equipped with a magnetic stir bar, and a side-arm adapter with a Kontes high vacuum valve and a 24/40 septum, is flame-dried under vacuum (0.3 mm Hg), then (in the glovebox) charged with 10.0 mg of the ligand IV, 5.0 mg Ni(1,5-cyclooctadiene)$_2$ (Aldrich) and 106 mg B(C$_6$F$_5$)$_3$ (Strem). On the Schlenk line, the flask is evacuated and refilled with ethylene, then charged with 100 mL dry, deoxygenated toluene while being stirred at 21° C. After 30 min., the reaction is quenched by the addition of MeOH and acetone. The white flocculent polyethylene which separates is isolated by vacuum filtration and dried in vacuo (0.4 mm Hg, 6 h) to yield polyethylene.

Synthesis of Supported Catalyst

Example 97

Synthesis of the Supported Nickel Complex D3. A flame dried Schlenk flask was charged with the imine/triazole complex D3 (15.5 mg, 31.2 μmol) and MAO treated silica (0.509 g, purchased from Witco TA 02794/HL/04) in an Ar filled dry box. The flask was immersed in an ice water bath under Ar, then CH$_2$Cl$_2$ (15 mL) was added. The resulting suspension was stirred at 0° C. for 1 hour then the solvent was removed via filter paper-tipped cannula and then in vacuo at 0° C. to afford supported D3.

Polymerization

Example 98

A 500 mL flame dried round bottom flask fitted with a gas adapter was charged with the supported catalyst prepared in example 97 (152 mg. 9.2 μmol Ni) in an Ar filled dry box. The flask was removed from the dry box and evacuated and refilled with 1 atm of ethylene, then toluene (100 mL) was immediately added. The resulting suspension was stirred vigorously under 1 atm of ethylene at room temperature for 2 h 15 min. The reaction was quenched by the sequential addition of acetone, MeOH and 6 N HCl. The precipitated polymer was isolated by vacuum filtration, washed a second time with HCl/MeOH, filtered and dried in vacuo at 80° C. to afford 0.871 g of polyethylene (1,500 TO/h). GPC: M$_n$=4,570, M$_w$=123,000; $^1$H NMR: (M$_n$=4,936; 7.6 branches/1000 carbons).

The invention has been described above in detail with particular reference to preferred embodiments thereof, but it will be understood that variations and modifications other than as specifically described herein can be effected within the spirit and scope of the invention. Moreover, all patents and literature references or other references herein are hereby incorporated by reference.

We claim:

1. A batch or continuous process for the polymerization of olefins, comprising contacting one or more monomers selected from compounds of the formula RCH=CHR$^1$ with a Group 8–10 transition metal complex of a ligand of the formula VI, XII, IX, XIII, XV, or XXII and optionally a Bronsted or Lewis acid,

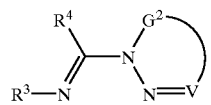
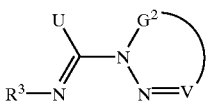
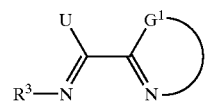
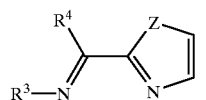
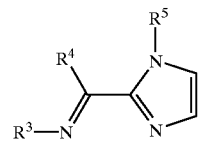
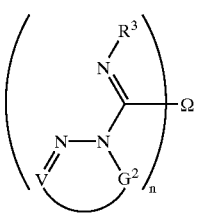

wherein R and R$^1$ are independently H, hydrocarbyl, fluoroalkyl, or R and may be linked to form a cyclic olefin;

R$^3$ is hydrocarbyl or substituted hydrocarbyl;

R$^4$ is H, hydrocarbyl, substituted hydrocarbyl, or silyl;

R$^5$ is hydrocarbyl or substituted hydrocarbyl;

Z is O or S;

U is —OR$^{10}$, —SR$^{10}$, —SeR$^{10}$ or —NR$^{10}$R$^8$, wherein R$^{10}$ and R$^8$ are each independently selected from H, hydrocarbyl, substituted hydrocarbyl, or silyl, and in addition R$^{10}$ and R$^8$ may collectively form a ring with nitrogen;

G$^1$ is hydrocarbyl or substituted hydrocarbyl and may comprise a carbocyclic or heterocyclic ring, thereby forming a 5-membered or 6-membered heterocyclic ring comprising G$^1$, C, and N;

G$^2$ is hydrocarbyl or substituted hydrocarbyl and may comprise a carbocyclic or heterocyclic ring, thereby forming a 5-membered or 6-membered heterocyclic ring comprising G$^2$, V, N, and N;

V is —CR$^6$, N, or —PR$^6$R$^9$; wherein, R$^6$ and R$^9$ are each independently selected from H, hydrocarbyl, substituted hydrocarbyl, silyl or heteroatom connected hydrocarbyl, and in addition, R$^6$ and R$^9$ may collectively form a ring with phosphorus;

Ω is hydrocarbyl or substituted hydrocarbyl; and, n is an integer between 2 and 6.

2. The process of claim 1 wherein the monomer of the formula RCH=CHR$^1$ is selected from ethylene, propylene, 1-butene, 1-hexene, and 1-octene.

3. The process of claim 1 wherein the group 8–10 transition metal is nickel.

4. The process of claim 3 wherein a Lewis acid is used, and said Lewis acid is methylaluminoxane.

5. The process of claim 4 wherein the ligand of formula VI is selected from:

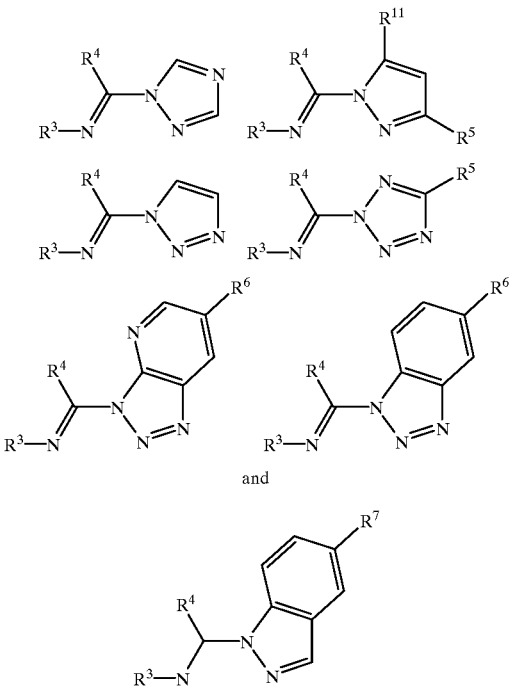

and

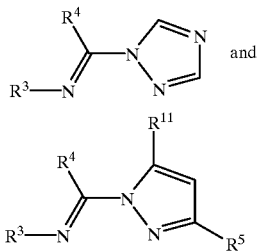

wherein R³ is hydrocarbyl or substituted hydrocarbyl;
R⁴ is H, hydrocarbyl, substituted hydrocarbyl, or silyl;
R⁵, R⁶ and R¹¹ are independently H, hydrocarbyl, or substituted hydrocarbyl;
R⁷ is H, hydrocarbyl, substituted hydrocarbyl, or NO₂.

6. The process of claim 5 wherein the ligand of formula VI is selected from:

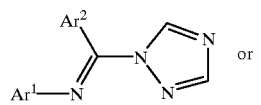

wherein R³ is hydrocarbyl or substituted hydrocarbyl;
R⁴ is H, hydrocarbyl, substituted hydrocarbyl, or silyl; and,
R⁵ and R¹¹ are independently H, hydrocarbyl, or substituted hydrocarbyl.

7. The process of claim 6 wherein the ligand of formula VI is

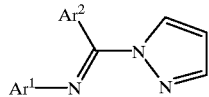

or

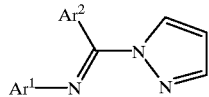

wherein Ar¹ is 2,6-dimethylphenyl or 2,6-diisopropylphenyl; and, Ar² is phenyl or 1-naphthyl.

8. The process of claim 4 wherein the ligand of formula XII is selected from:

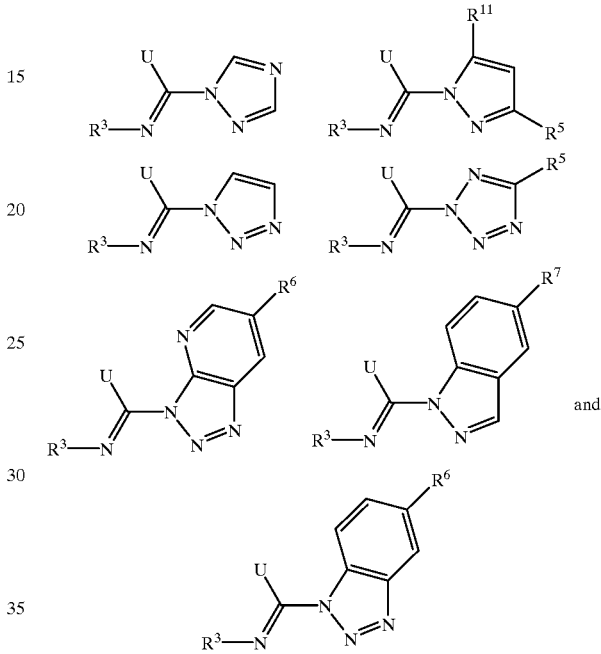

and

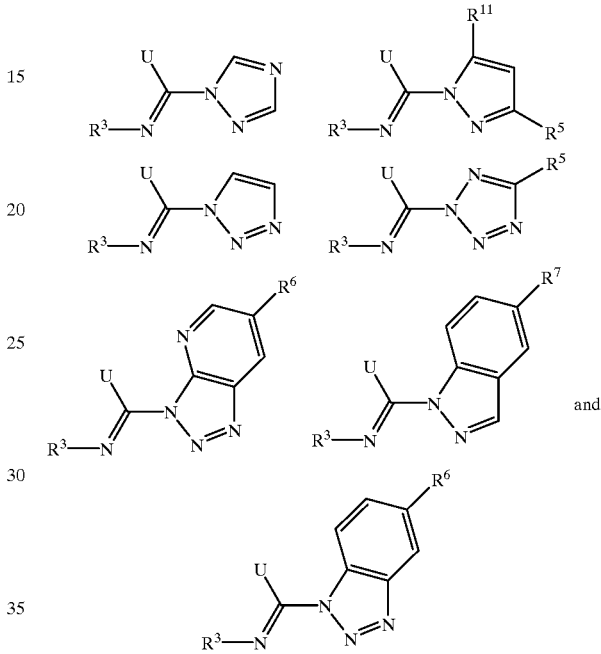

wherein R³ is hydrocarbyl or substituted hydrocarbyl;
U is —OR¹⁰, —SR¹⁰, —SeR¹⁰ or —NR¹⁰R⁸, wherein R¹⁰ and R⁸ are each independently selected from H, hydrocarbyl, substituted hydrocarbyl, or silyl, and in addition R¹⁰ and R⁸ may collectively form a ring with nitrogen;
R⁵, R⁶ and R¹¹ are independently H, hydrocarbyl, or substituted hydrocarbyl;
R⁷ is H, hydrocarbyl, substituted hydrocarbyl, or —NO₂.

9. The process of claim 8 wherein the ligand of formula XII is selected from:

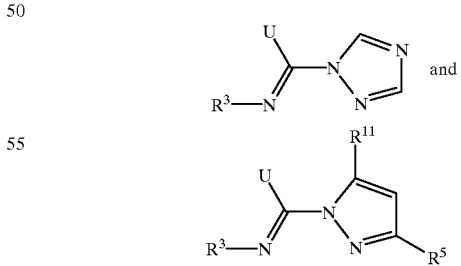 and wherein R³ is hydrocarbyl or substituted hydrocarbyl;
U is —OR¹⁰, —SR¹⁰, —SeR¹⁰ or —NR¹⁰R⁸, wherein R¹⁰ and R⁸ are each independently selected from H, hydrocarbyl, substituted hydrocarbyl, or silyl, and in addition R¹⁰ and R⁸ may collectively form a ring with nitrogen;

$R^5$ and $R^{11}$ are independently H, hydrocarbyl, or substituted hydrocarbyl.

10. The process of claim 4 wherein the ligand of formula IX is selected from:

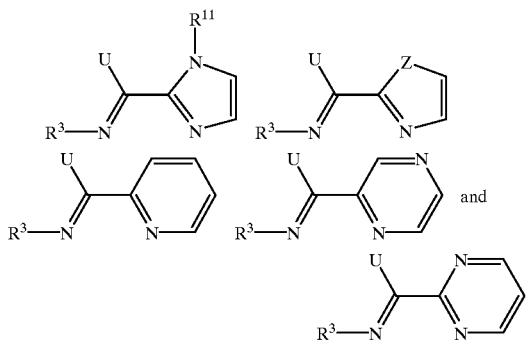

wherein $R^3$ is hydrocarbyl or substituted hydrocarbyl;
$R^{11}$ is hydrocarbyl, or substituted hydrocarbyl;
U is $-OR^{10}$, $-SR^{10}$, $-SeR^{10}$ or $-NR^{10}R^8$, wherein $R^{10}$ and $R^8$ are each independently selected from H, hydrocarbyl, substituted hydrocarbyl, or silyl, and in addition $R^{10}$ and $R^8$ may collectively form a ring with nitrogen; and
Z is oxygen or sulfur.

11. The process of claim 4 wherein the ligand is of formula XXII and Ω is selected from:

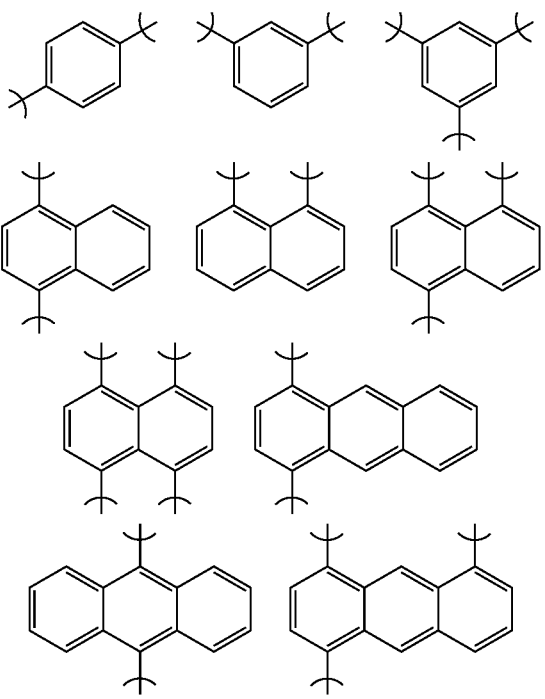

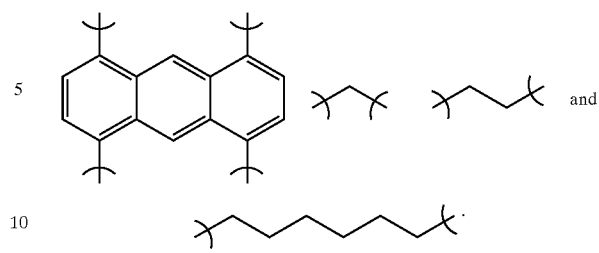

12. The process of claim 11 wherein the ligand of formula XXII is selected from:

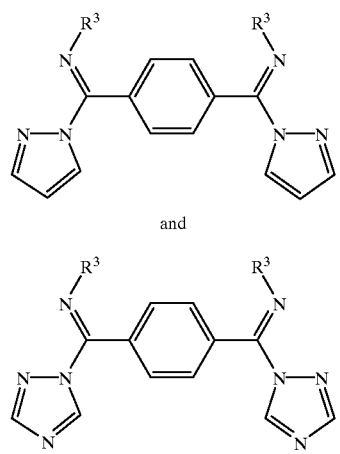

wherein $R^3$ is 2,6-disubstituted phenyl.

13. The process of claim 4 wherein the polymerization is conducted in an inert solvent.

14. The process of claim 5, 8, 10 or 11 wherein the polymerization is conducted in an inert solvent.

15. The process of claim 4 wherein the transition metal olefin polymerization catalyst system is attached to a solid support.

16. The process of claim 5, 8, 10, or 11 wherein the transition metal olefin polymerization catalyst system is attached to a solid support.

17. The process of claim 15 wherein the polymerization is conducted in an inert solvent.

18. The process of claim 16 wherein the polymerization is conducted in an inert solvent.

19. The process of claim 15 wherein the polymerization is conducted in the gas phase.

20. The process of claim 16 wherein the polymerization is conducted in the gas phase.

* * * * *

UNITED STATES PATENT AND TRADEMARK OFFICE
CERTIFICATE OF CORRECTION

PATENT NO. : 6,844,404 B2
DATED : January 18, 2005
INVENTOR(S) : James Allen Ponasik, Jr. et al.

It is certified that error appears in the above-identified patent and that said Letters Patent is hereby corrected as shown below:

<u>Column 46,</u>
Line 37, should read as follows:
-- fluoroalkyl, or R and $R^1$ may be linked to form a cyclic --

Signed and Sealed this

Twelfth Day of April, 2005

JON W. DUDAS
*Director of the United States Patent and Trademark Office*